US010709410B2

(12) United States Patent
Meiler et al.

(10) Patent No.: US 10,709,410 B2
(45) Date of Patent: Jul. 14, 2020

(54) X-RAY IMAGING COMPONENT COMMUNICATION SYSTEM AND PROTOCOL

(71) Applicant: Varex Imaging Corporation, Salt Lake City, UT (US)

(72) Inventors: Michael Meiler, Salt Lake City, UT (US); Steven E. Hebeler, Salt Lake City, UT (US); Michelle Richmond, Salt Lake City, UT (US); Lori Fry, Salt Lake City, UT (US)

(73) Assignee: VAREX IMAGING CORPORATION, Salt Lake City, UT (US)

( * ) Notice: Subject to any disclaimer, the term of this patent is extended or adjusted under 35 U.S.C. 154(b) by 92 days.

(21) Appl. No.: 16/130,999

(22) Filed: Sep. 13, 2018

(65) Prior Publication Data

US 2019/0076111 A1     Mar. 14, 2019

Related U.S. Application Data

(60) Provisional application No. 62/558,299, filed on Sep. 13, 2017.

(51) Int. Cl.
*H04N 5/32* (2006.01)
*A61B 6/00* (2006.01)
(Continued)

(52) U.S. Cl.
CPC .............. *A61B 6/566* (2013.01); *A61B 6/032* (2013.01); *G01T 1/247* (2013.01); *G16H 40/67* (2018.01); *H04L 67/12* (2013.01); *H04N 5/32* (2013.01)

(58) Field of Classification Search
CPC ......... H04L 67/12; A61B 6/032; A61B 6/566; G01T 1/247; H04N 5/32
See application file for complete search history.

(56) References Cited

U.S. PATENT DOCUMENTS 6,275,869 B1    8/2001   Sieffert et al.
2002/0176535 A1*  11/2002  Dixon .................... A61B 6/00
                                                              378/62
(Continued)

FOREIGN PATENT DOCUMENTS

JP     2015146916 A    8/2015
JP     6305085 B2 *    4/2018 ............... A61B 6/00

OTHER PUBLICATIONS

International Search Report and Written Opinion dated Jan. 18, 2019 in International Application No. PCT/US2018/050970.

*Primary Examiner* — David P Porta
*Assistant Examiner* — Fani Boosalis
(74) *Attorney, Agent, or Firm* — Maschoff Brennan

(57) ABSTRACT

A method of communicating between imaging components of an X-ray imaging system may include determining, by an initiator imaging component, whether a target imaging component is a primary manufacturer imaging component (PMIC). Responsive to the target imaging component not being the PMIC, the method may include generating a communication message including a communication packet according to a packet protocol. Responsive to the target imaging component not being the PMIC, the method may also include sending the communication message to the target imaging component as a secondary manufacturer imaging component. Responsive to the target imaging component being the PMIC, the method may include generating a message including a header packet and one or more data packets according to a message protocol. Responsive to the target imaging component being the PMIC, the method may also include sending the message to the target imaging component as the primary manufacturer imaging component.

20 Claims, 13 Drawing Sheets

(51) Int. Cl.
*G01T 1/24* (2006.01)
*A61B 6/03* (2006.01)
*H04L 29/08* (2006.01)
*G16H 40/67* (2018.01)

(56) References Cited

U.S. PATENT DOCUMENTS

2003/0214953 A1 11/2003 El-Demerdash et al.
2010/0150153 A1 6/2010 Cheswick
2014/0112437 A1 4/2014 Schmitz et al.

* cited by examiner

X-RAY IMAGING COMPONENT COMMUNICATION SYSTEM AND PROTOCOL

CROSS-REFERENCE TO RELATED APPLICATIONS

This application claims the benefit of U.S. Provisional Patent Application No. 62/558,299 filed Sep. 13, 2017, which is incorporated herein by reference in its entirety.

BACKGROUND

Unless otherwise indicated herein, the approaches described in this section are not prior art to the claims in this disclosure and are not admitted to be prior art by inclusion in this section.

The present disclosure generally relates to X-ray imaging systems, including embodiments relating to communication between components of X-ray imaging systems. X-ray imaging systems, such as Computed Tomography (CT) systems, typically include an X-ray tube, a detector, and a support structure, such as a gantry. In operation, an imaging table, on which a patient or object is positioned, is located between the X-ray tube and the detector. A generator provides power and/or timing signals to the X-ray tube. The X-ray tube emits radiation, such as X-rays, toward the object and the radiation passes through the object on the imaging table and then impinges on the detector. As radiation passes through the object, internal structures of the object cause spatial variances in the radiation received at the detector. The detector transmits data representative of the received radiation to a computing system. The computing system translates the radiation variances into an image, which may be used to evaluate the internal structure of the object. The object may include, but is not limited to, a patient in a medical imaging procedure, an inanimate object in a package scanner, or some other component, device or material under analysis. X-ray imaging systems may include one or more control systems configured to communicate with and/or operate imaging components within an X-ray imaging system, such as the X-ray tube, the detector, the gantry, the imaging table and/or other imaging components.

The claimed subject matter is not limited to embodiments that solve any disadvantages or that operate only in environments such as those described above. This background is only provided to illustrate examples of where the present disclosure may be utilized.

DETAILED DESCRIPTION OF SOME EXAMPLE EMBODIMENTS

Figure 1:
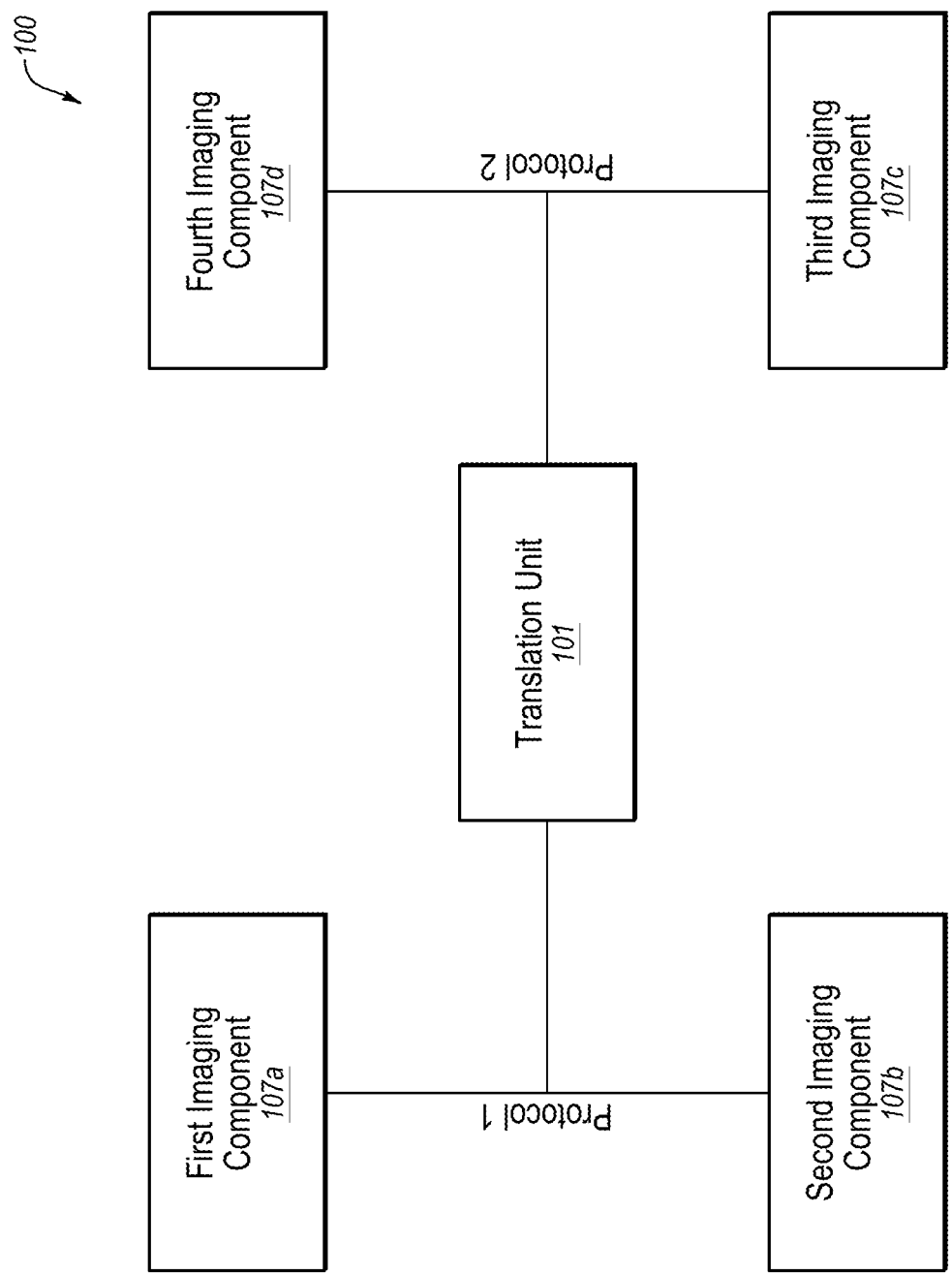
FIG. 1 illustrates an example X-ray imaging system that includes four imaging components communicating using two communication protocols.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Numbers provided in flow charts and processes are provided for clarity in illustrating steps and operations and do not necessarily indicate a particular order or sequence. Unless otherwise defined, the term "or" can refer to a choice of alternatives (e.g., a disjunction operator, or an exclusive or) or a combination of the alternatives (e.g., a conjunction operator, and/or, a logical or, or a Boolean Oreg.). As used herein, "bus" refers to any communication channel (e.g., in the open system interconnection [OSI]) model), and "communication protocol" or "protocol" refers to a defined set of rules that determine how data is transmitted in telecommunications or computer networking.

Reference will be made to drawings and specific language will be used to describe various aspects of the disclosure. Using the drawings and description in this manner should not be construed as limiting its scope. Additional aspects may be apparent in light of the disclosure, including the claims, or may be learned by practice.

X-ray imaging systems may include various components, such as one or more of: an X-ray tube, a detector, a tube control unit (TCU), a heat exchanger, an authentication board or authentication daughter board (ADB), a tube auxiliary unit (TAU), a high voltage generator, a system control unit (e.g., a host system), and a support structure, such as a gantry.

In some embodiments, the X-ray imaging system components may include one or more imaging components used by a primary manufacturer (PM) imaging manufacturing company, also referred to as a PM imaging component (PMIC), and one or more imaging components supplied by secondary manufacturer (SM) manufacturing companies, also referred to as a SM imaging component (SMIC). For example, the X-ray tube, the detector, the TCU, the authentication board(s) or the ADB, and the TAU may be classified as PMICs (e.g., imaging components from the primary manufacturer) and the generator, the system control unit, and the gantry may be classified as SMICs (e.g., imaging components from a second manufacturer and/or different manufacturers). Although, the examples refer to PMICs and SMICs for purposes of illustration, more than two manufacturers' imaging components (e.g., a third manufacturer's imaging components and/or a fourth manufacturer's imaging components that are classified as SMICs) may also be used in the X-ray imaging system.

Although the terms "primary manufacturer"/"primary manufacturer imaging component" and "secondary manufacturer"/"secondary manufacturer imaging component" are used herein, it should be understood that the imaging components may be manufactured by the same manufacturer. Rather than the source of an imaging component, the reference to the imaging component being a primary manufacturer imaging component or secondary manufacturer imaging component may be understood to indicate different technical characteristics and/or capabilities of the respective imaging components. The primary manufacturer imaging component may have a first set of technical characteristics and/or capabilities, and the secondary manufacturer imaging component may have a second, different, set of technical characteristics and/or capabilities. The "primary" and "secondary" manufacturer imaging components may be technically incompatible in some way (even if they are available from the same manufacturer).

During operation of an X-ray imaging system, status and/or command messages may be sent between the various imaging components. For example, the TCU may send a temperature status request to the TAU. In response, the TAU may transmit a status message that includes data that indicates the temperature of the TAU.

The ADB may be used to authenticate imaging components of X-ray imaging systems. The ADB may include cryptographic authentication hardware/firmware that permits encrypted communication with the imaging components (e.g., the system control unit and/or the TAU). Although, "ADB" is referred to as a separate component, the functionality of ADB may be integrated into circuits of the PMIC or the ADB can be a separate component that is coupled to or installed with the SMIC. In some examples, the ADB can be manufactured by the PM and provided to the SM for use with the SMIC. For example, the TAU and/or the system control unit may also include cryptographic authentication hardware/firmware that permits encrypted communication with the ADB. In some embodiments, the TAU may be attached to the X-ray tube and the ADB may request verification of the X-ray tube via the TAU. For example, a replacement X-ray tube may be installed and the ADB may request verification of the replacement X-ray tube via the TAU. The system control unit may control rotation of the gantry, the detector, the X-Ray Tube and the generator etc. The system control unit may also communicate with the ADB and provide commands for the ADB to perform authentication of one or more imaging components.

In some embodiments, an X-ray imaging system may use one or more communication buses to interconnect the various imaging components, and one or more communication protocols to allow communication between and with the various imaging components. Communication using different communication buses and/or communication protocols presents a variety of problems, including but not limited to increased time to implement X-ray imaging systems, incompatibility issues between the various imaging components, and message translation conflicts. Additionally, communication between imaging components using different buses and/or different communication protocols may increase the cost and size of components within an X-ray imaging system due to the need for relatively complex translation units and/or translation software needed to accommodate the different protocols.

FIG. 1 illustrates an example X-ray imaging system 100 that includes four imaging components 107a-d communicating using two communication protocols (protocol "1" and protocol "2"). The imaging components 107a-d communicating using the two communication protocols may use at least one translation unit 101 so as to permit communication between a first imaging component 107a and second imaging component 107b that communicate using protocol 1 and a third imaging component 107c and a fourth imaging component 107d that communicate using protocol 2. The translation unit 101 may provide additional logic so as to convert protocol 1 to protocol 2 and vice versa.

Figure 2:
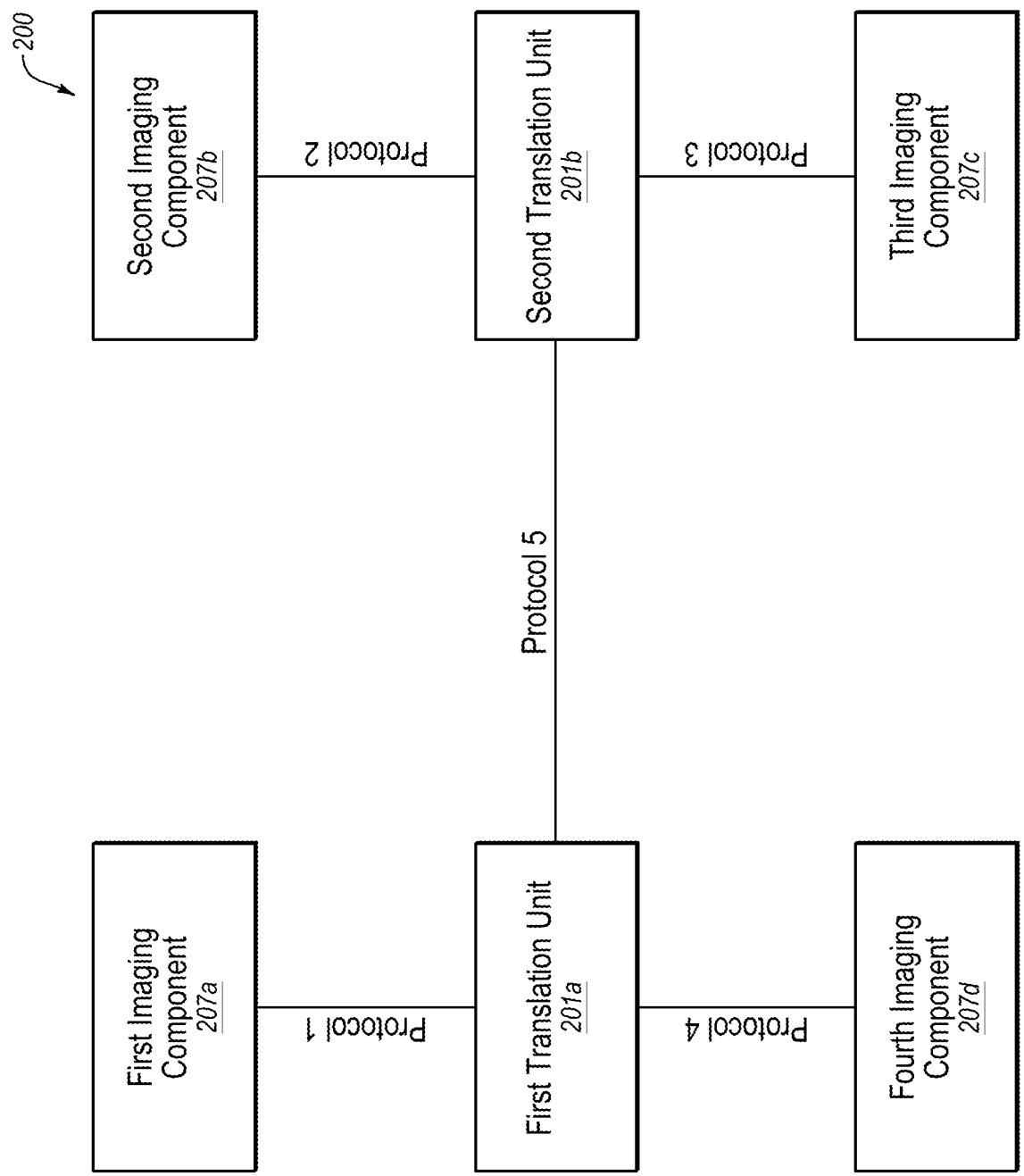
FIG. 2 illustrates an example X-ray imaging system that includes four imaging components communicating using four communication protocols.

FIG. 2 illustrates an example X-ray imaging system 200 that includes four imaging components 207a-207d communicating using four communication protocols (protocol "1", protocol "2", protocol "3", and protocol "4"). For example, a first imaging component 207a may communicate using protocol 1, a second imaging component 207b may communicate using protocol 2, a third imaging component 207c may communicate using protocol 3, and a fourth imaging component 207d may communicate using protocol 4. The X-ray imaging system 200 may also include at least two translation units 201a-b that communicate using a fifth communication protocol (protocol "5").

Messages sent from any of the imaging components 207a-d to any of the other imaging components 207a-d may be translated at least once, and possibly up to two times. For example, a message transmitted by the first imaging component 207a to the fourth imaging component 207d may be translated from protocol 1 to protocol 4 by a first translation unit 201a. As another example, a message transmitted by the second imaging component 207b to the fourth imaging component 207d may be translated from protocol 2 to protocol 5 by a second translation unit 201b. Additionally, the first translation unit 201a may translate the message from protocol 5 to protocol 4.

The translation of messages may increase processing delays, translation errors, response times, control times for X-ray imaging systems, and other issues. Likewise, with the amount of data being collected by X-ray imaging systems ever increasing, these X-ray imaging systems may not be able to process and/or send messages fast enough to handle the large amounts of data being collected, thereby creating a bottleneck in efficient imaging operation and processing.

In some embodiments, to reduce the number of, or even eliminate, translation units in an X-ray imaging system, the various imaging components may communicate using a flexible communication protocol and/or a flexible communication bus. Implementation of the flexible communication protocol and/or the flexible communication bus may increase reliability, increase communication consistency, and reduce complexity of an X-ray imaging system. Likewise, implementation of the flexible communication protocol and/or the flexible communication bus may reduce the amount of time needed to replace and/or upgrade one or more imaging components of an X-ray imaging system since the imaging component can communicate using the same flexible communication protocol. Additionally, implementation of the flexible communication protocol and/or the flexible communication bus may permit unencrypted (e.g., a non-secure and/or an open) messages to be sent to various imaging components while encrypted (e.g., a secure and/or closed) messages are sent to different imaging components.

In an example embodiment, the flexible communication protocol having a packet protocol (e.g., a secondary manufacturer specific protocol, open protocol, non-secure protocol, or fixed protocol) and a message protocol (e.g., a primary manufacturer specific protocol or secure protocol) is provided. The packet protocol might be used for communication between PMICs and the SMICs expecting the packet protocol or a specific packet format. Furthermore, the packet protocol may be used for unencrypted communication between the PMICs and the SMICs. In addition, the packet protocol may be used for any communication that occurs between the SMICs. In contrast, the message protocol may be used for communication that occurs between the PMICs. Additionally, the message protocol may be used for encrypted communication between the PMICs.

In some embodiments, the packet protocol can be implemented to permit communication via a single packet to occur between the PMICs and the SMICs and/or between SMICs. In this way, the packet protocol uses a standard communication protocol for the SMICs to communicate across the flexible communication bus with one or more of the PMICs and/or one or more of the SMICs. Similarly, the message protocol can be implemented to permit communication between the PMICs via a header packet (or envelope) and one or more data packets forming a message with multiple packets.

The system control unit may be communicatively coupled to various host devices via a host bus, which may operate separate from the flexible communication bus. In some embodiments, the flexible communication protocol can be implemented to permit unauthenticated SMICs to remain powered on in the X-ray imaging system without being turned off due to lack of authentication so as to meet various governmental requirements of X-ray imaging systems. In these and other embodiments, the unauthenticated SMICs may transmit messages that may be received but not processed by PMICs. For example, a replacement X-ray tube including an ADB may be installed in an X-ray imaging system. The X-ray tube may fail authentication and continue to be powered on and send messages to PMICs using the flexible communication protocol without the PMICs processing the messages.

In some embodiments, the flexible communication protocol can be implemented to permit a portion of a message generated according to the message protocol to be transmitted by a PMIC prior to and after a message generated according to the packet protocol is transmitted (e.g., packets from the message protocol can be interspersed with packets from the packet protocol). For example, a message generated according to the message protocol may include a header packet and six data packets. The header packet and two of the data packets may be transmitted by a PMIC. A message generated according to the packet protocol may be transmitted after the header packet and the two data by the PMIC. Subsequently, the remaining four data packets may be transmitted after the message generated according to the packet protocol.

In an example embodiment, communication between the PMICs and the SMICs may occur via a CAN bus (e.g., the flexible communication bus may include a CAN bus). Messages communicated via the CAN bus may be generated with specific field occupying specific bits as discussed in more detail below in relation to FIGS. 3-5. For example, a CAN frame may include one hundred twenty eight bits of which ninety three are set according to embodiments disclosed herein.

In some embodiments, communication between the PMICs and the SMICs may occur in network, transport, session, presentation, and/or application layers of an open system interconnection (OSI) model. Meanwhile, CAN communication may occur in a physical layer and a data link layer of the OSI model. For example, a source field (334 FIG. 3) and/or a destination field (336 FIG. 3) in a communication packet (300 FIG. 3) may be used in the network layer of the OSI model. As another example, one or more command fields (344a-344b FIG. 3) in the communication packet (300 FIG. 3) may be used in the presentation and/or the application layers in the OSI model. Furthermore, a packet number field (340 FIG. 3) may be used in the presentation and/or the application layer of the OSI model. Likewise, a data field (342a-342f) in a communication packet (300 FIG. 3) may be used in the application layer and/or the presentation layer in the OSI model. Additionally, a SM command code field (338 FIG. 3) may be used in the session layer of the OSI model.

In some embodiments, a PM source field (450 FIG. 4 and/or FIG. 5) and/or a PM destination field (452 FIG. 4 and/or FIG. 5) in a header packet (400 FIG. 4) and/or a data packet (500 FIG. 5) may be used in the network layer of the OSI model. As another example, a PM command code field (454 FIG. 4 and/or FIG. 5) in the header packet (400 FIG. 4) and/or the data packet (500 FIG. 5) may be used in the session layer of the OSI model. As yet another example, a CRC high field (458a FIG. 4) and/or a CRC low field (458b FIG. 4) may be used in the transport layer of the OSI model. Furthermore, a response code field (462 FIG. 4), an acknowledge field (464 FIG. 4), a high byte total message data bytes field (466 FIG. 4), low byte total message data bytes field (468 FIG. 4), a packet number field (340 FIG. 4), and/or a data packet number field (574 FIG. 5) may be used in the session layer of the OSI model. Likewise, a data field (342a-342f FIG. 5) in a data packet (500 FIG. 5) may be used in the application layer in the OSI model. Additionally, an encryption field (460 FIG. 4) may be used in the presentation layer.

Figure 6:
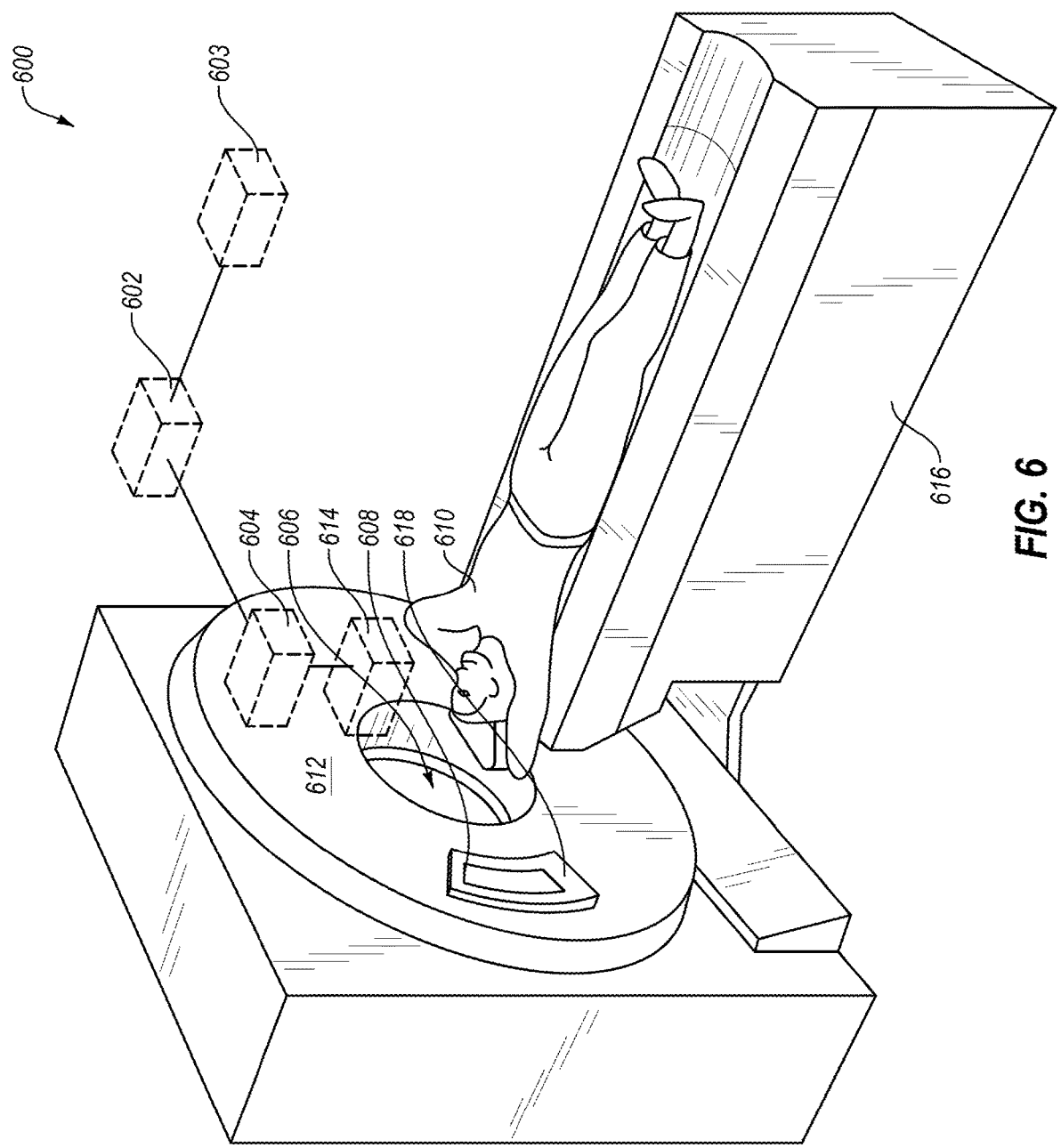
FIG. 6 is a perspective view of one example of an X-ray imaging system that may be used to acquire image data and process, display, and/or analyze the image data.

FIG. 6 is a perspective view of one example of an X-ray imaging system 600 (herein the system 600) that may be used to acquire image data and process, display, and/or analyze the image data, in accordance with one or more embodiments disclosed herein. The system 600 may be referred to as an X-ray imaging system, which may be, for example, a CT system. The system 600 is one example of an operating environment where the concepts described in this disclosure may be implemented, but it is not limiting. The concepts described may be implemented in any one of a number of different X-ray imaging system types.

Referring to FIG. 6, the system 600 may include a support structure, such as a gantry 612, that includes an X-ray source assembly 614 that is configured to generate and project X-rays toward a collimator (not shown) or a detector assembly 618 positioned on an opposite side of the gantry 612. The system 600 may include an actuating table 616 to receive and position a patient (or another object to be scanned depending on the application) denoted at 610. For example, the actuating table 616 may move the patient 610 at least partially through an opening 606 of the gantry 612 such that X-rays generated by the X-ray source assembly 614 pass through the patient 610 and are received by the detector assembly 618 to obtain information (e.g., X-ray projection data) about the patient 610.

The X-ray source assembly 614 may include an X-ray tube (not shown) to generate X-rays in a manner that is well known. In other examples, the X-ray source assembly may be another type of X-ray source, such as a linear accelerator. The detector assembly 618 may include one or more detectors 608 configured to detect the X-rays that pass through the patient 610, also in a manner that is well known.

The X-ray source assembly 614 may be communicatively coupled to a TCU, denoted at 604. The TCU 604 may be communicatively coupled to a system control unit denoted at 602. In general, the system control unit 602 may interface with and control various components of the system 600. In addition, the TCU 604 may interface with the X-ray source assembly 614 so as to provide, for example, control signals to the X-ray source assembly 614. The control signals provided by the TCU 604 to the X-ray source assembly 614 may include signals to control, for example, electron steering magnetics and focusing components in an X-ray tube of the X-ray source assembly 614. In some configurations, a generator (an example of which is denoted in FIG. 7 at 728, which may be a component on the gantry 612) may provide, for example, power and/or timing signals to the X-ray source assembly 614, for further control of the X-ray tube and resulting X-ray generation. The system control unit 602 may interface with the generator so as to allow operator control by providing, for example, control signals to the generator. The generator ADB may include a plug in board for the generator to communicate with the other imaging components.

In the illustrated configuration of FIG. 6, the TCU 604 is configured so as to be positioned on and coupled to the gantry 612 in a manner such that it is physically separate from the X-ray source assembly 614. In other configurations, the TCU 604 may be positioned at other portions of the system 600, or it may be integrated with the X-ray source assembly 614.

During a scan of the patient 610 to acquire X-ray projection data, the actuating table 616 may position a portion of the patient 610 to be analyzed at least partially through the opening 606 of the gantry 612. During the scan, the gantry 612 and the components mounted thereon may rotate about a center of rotation, and the X-ray source assembly 614 may emit X-rays that travel through the patient 610 to the detector assembly 618. The gantry 612 and the actuating table 616 may be communicatively coupled to the system control unit 602. Rotation of the gantry 612 and actuation of the actuating table 616 may be at least partially controlled by the system control unit 602 via issuance of appropriate control signals. As illustrated in FIG. 6, a gantry is used in the X-ray imaging system. In other examples, other functional or structural components may be used, such a C-arm in cardiovascular (CV) applications.

The system control unit 602 may receive the digital signals representative of the radiation received at the detector assembly 618, which may be processed or stored in memory. The system control unit 602 may also receive commands and scanning parameters from an operator via a console 603 that has a suitable operator interface, such as a display, keyboard, mouse, or any other suitable interface components (not shown). An associated display may allow the operator to observe images and other data from the system control unit 602. The operator may make adjustments to the operation of the X-ray source assembly 614 via the system control unit 602. In some configurations, the operator may make adjustments to the operation of the generator to provide, for example, power and/or timing signals to the X-ray source assembly 614.

Although the system 600 illustrated is configured to analyze a patient as denoted at 610, in alternative configurations the system 600 may be configured to analyze other types of samples or objects. In such circumstances, the actuating table 616 and/or the gantry 612 may be adapted based on the size and shape of the object under analysis.

FIG. 6 illustrates a system 600 configured as a CT system. In other examples, the system 600 can be configured as a radiological system, a mammography, fluoroscopy system, a C-arm system, a security or inspection system, a non-destructive testing (NDT) system, a linear accelerator, X-ray systems used in security and inspection systems, or other type of X-ray imaging system.

Figure 7:
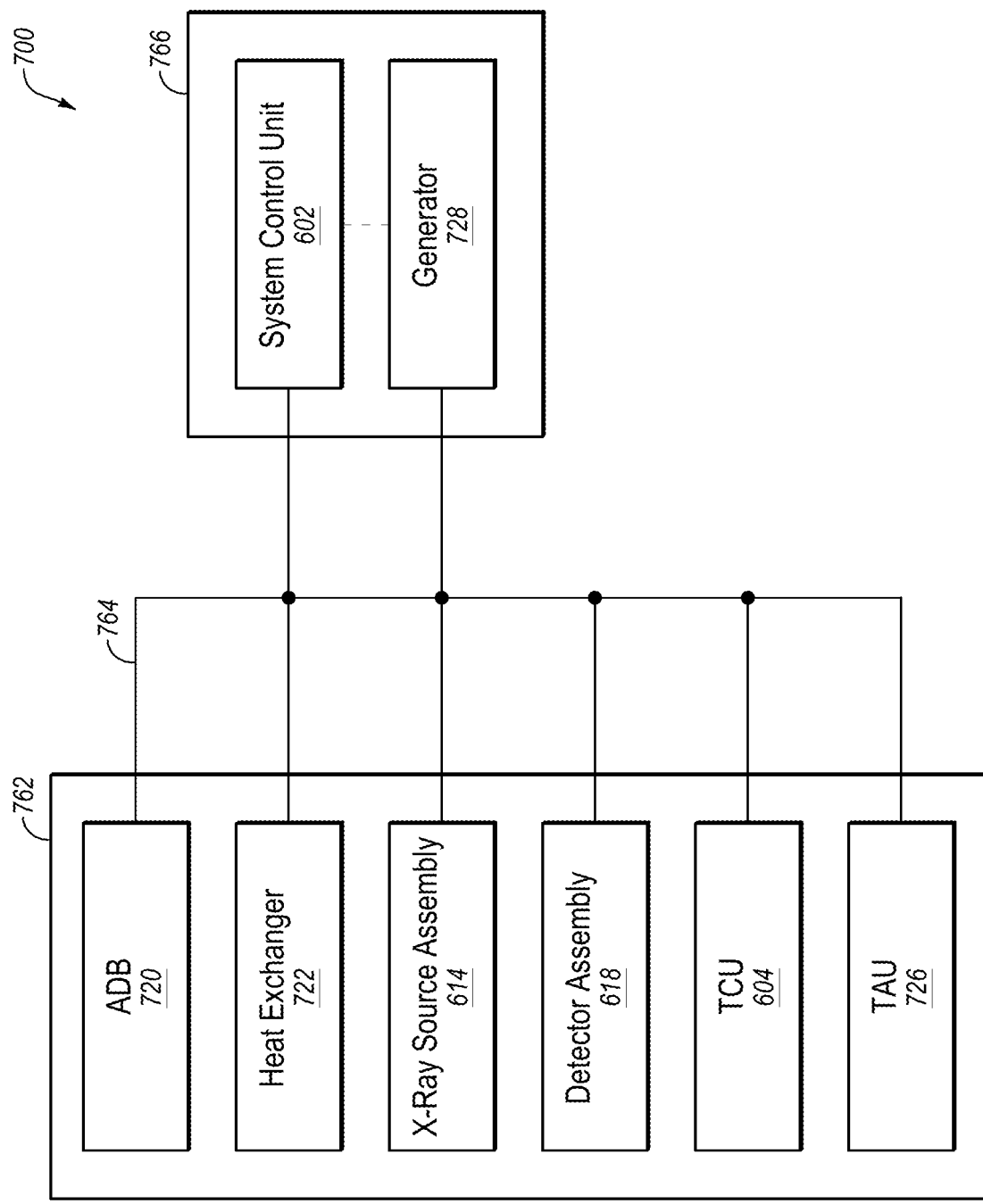
FIG. 7 illustrates a block diagram of an embodiment of an X-ray imaging system.

FIG. 7 illustrates a block diagram of an embodiment of an X-ray imaging system 700 (herein the system 700), which may permit communication via a flexible communication bus, denoted at 764, in accordance with one or more embodiments disclosed herein.

Referring to FIG. 7, the system 700 may include a secondary portion 766 and a primary portion 762. The primary portion 762 may include, for example, an ADB 720, one or more heat exchangers 722, an X-ray source assembly 614, a detector assembly 618, a TCU 604, and a TAU 726. The secondary portion 766 may include, for example, a system control unit 602, and a generator 728. The X-ray source assembly 614, the detector assembly 618 and system control unit 602 may be the same as or similar to the X-ray source assembly 614, the detector assembly 618, and the system control unit 602 discussed above in relation to FIG. 6. For purposes of illustration, the imaging components within the primary portion 762 may be manufactured by a first manufacturer and the imaging components within the secondary portion 766 may be manufactured by one or more different manufacturers (e.g., a second manufacturer, a third manufacturer, etc.). For example, the system control unit 602 may be manufactured by the second manufacturer and the generator 728 may be manufactured by the third manufacturer. As another example, system control unit 602 and the generator 728 may be manufactured by the second manufacturer.

As is shown in the example implementation of FIG. 7, the imaging components within the primary portion 762 may be communicatively coupled with the imaging components within the secondary portion 766 via the flexible communication bus 764. The various imaging components (the PMICs and the SMICs) of the system 700 may thus communicate using the flexible communication protocol. In some embodiments, the flexible communication bus 764 may include a controller area network (CAN) bus, transmission control protocol/Internet protocol (TCP/IP) bus, inter-integrated circuit (I2C) bus, serial peripheral interface (SPI) bus, or any other suitable communication bus. CAN bus is a robust bus standard original designed for vehicles to allow microcontrollers and devices to communicate with each other in applications without a host computer. CAN bus can provide reliable communication on noisy communication channels (e.g., physical layer), which noisy communication can occur in imaging systems.

In an embodiment, the flexible communication protocol may include multiple sub-protocols. For example, the flexible communication protocol may include a packet sub-protocol (referred to herein as packet protocol), which may permit communication between the imaging components within the primary portion 762 and the imaging components within the secondary portion 766 of the system 700 via the flexible communication bus 764. Additionally, the packet protocol may permit communication between the imaging components within the secondary portion 766 of the system 700 via the flexible communication bus. As another example, the flexible communication protocol may include a message sub-protocol (referred to herein as message protocol), which may permit communication between the imaging components within the primary portion 762 of the system 700 via the flexible communication bus 764.

In some embodiments, the system control unit 602 may be employed as a command center for indirectly or directly controlling and/or monitoring the imaging components within the secondary portion 766 and/or the primary portion 762 of the system 700. In these and other embodiments, the system control unit 602 may include software, hardware, a console, and a display (not shown) that allows a user operator to, for example, monitor the status of the system 700, send commands to the various imaging components of the system 700, and/or to process the X-ray images captured by the system 700.

Additionally, the system control unit 602 may include a host ADB (not shown) in communication with the other imaging components of the system 700. The host ADB may be used to authenticate the imaging components within the secondary portion 766 of the system 700. Communication between the host ADB and the imaging components within the secondary portion 766 of the system 700 may occur in parallel to communication between the imaging components within the primary portion 762 and the imaging components within the secondary portion 766 of the system 700.

Furthermore, the system control unit 602 may be communicatively coupled to additional imaging components via a host bus (not shown). The system control unit 602 may receive commands for controlling and/or monitoring the imaging components within the secondary portion 766 and/or the primary portion 762 of the system 700 via the host bus. Communication with the system control unit 602 via the host bus may occur separate from communication between imaging components via the flexible communication bus 764.

In an embodiment, the TCU 604 may be communicatively coupled with the X-ray source assembly 614 via the flexible communication bus 764 so as to facilitate the exchange of control signals and/or data. By way of example, control signals may include signals to control electron steering magnetics and focusing components in an X-ray tube of the X-ray source assembly 614. The TAU 726 may also be communicatively coupled to the TCU 604 via the flexible communication bus 764 to facilitate the exchange of signals and/or data. In an embodiment, the TCU 604 may also be communicatively coupled to the system control unit 602 via the flexible communication bus 764. Accordingly, control signals and/or data may be transmitted between the TAU 726, the TCU 604, and the system control unit 602. In an example embodiment, the TAU 726 may provide the TCU 604 with data that is specific to an X-ray tube associated with the X-ray source assembly 614. Non-limiting examples of such data might include tube manufacture data, tube calibration data, control data, and/or tube operating data.

In an embodiment, the one or more heat exchangers 722 may also be communicatively coupled to the system control unit 602 via the flexible communication bus 764. In this way, the system control unit 602 can provide control signals to, or receive data from, the heat exchanger(s) 722. In an example embodiment, the heat exchanger 722 may be configured to dissipate heat generated by the X-ray source assembly 614 during operation of the system 700 and may provide the system control unit 602 with data that is specific to the heat dissipation. Such data might include current temperature of the X-ray source assembly 614, current level of heat dissipation, and/or any other status regarding the heat exchanger 722. In a similar fashion and depending on the configuration, the system control unit 602, in response to such status data, may control operation of the heat exchanger 722 via appropriate control signals. For example, adjustment of coolant flow and or operating temperature might be varied in accordance with appropriate control signals.

In an embodiment, the generator 728 may provide, for example, power and/or timing signals to the X-ray source assembly 614. The power and/or timing signals may also be used to the X-ray tube and resulting X-ray generation.

Figure 8:
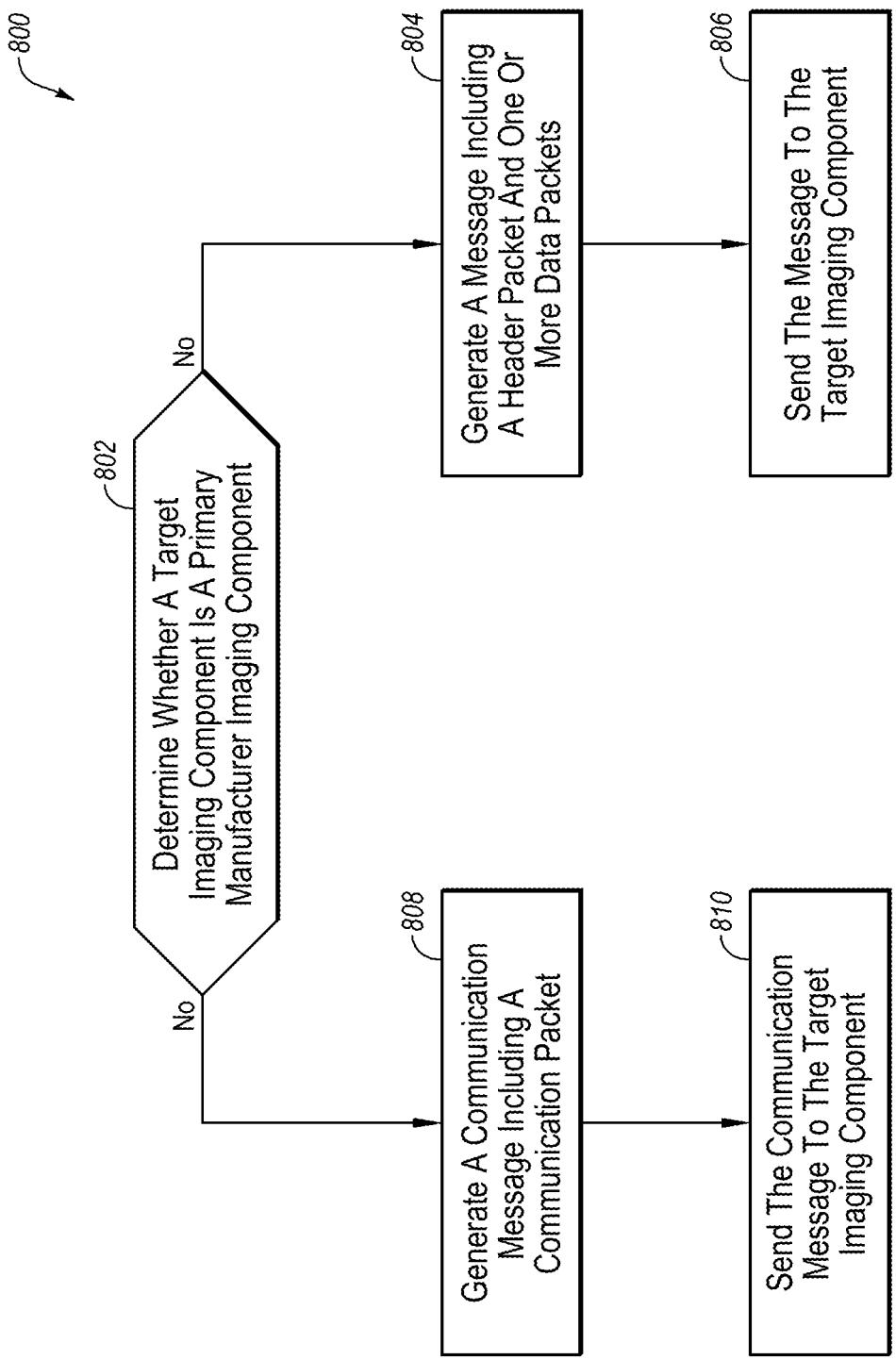
FIG. 8 is a flow chart illustrating an example method for communication between imaging components of an X-ray imaging system.

FIG. 8 is a flow chart illustrating an example method 800 for communication between imaging components of an X-Ray imaging system, in accordance with one or more embodiments disclosed herein. The method 800 may be performed by any suitable system, apparatus, or imaging component. For example, the systems 600 and 700 of FIGS. 6 and 7 may direct performance of one or more of the operations associated with the method 800. Although illustrated with discrete blocks, the steps and operations associated with one or more of the blocks of the method 800 may be divided into additional blocks, combined into fewer blocks, or may be eliminated completely, depending on the particular implementation. The method 800 may begin at block 802, where it is determined whether a target imaging component is a primary manufacturer imaging component. An initiator imaging component may determine whether the target imaging component is the primary manufacturer imaging component. In some embodiments, the initiator imaging component may determine whether an address of the receiving component is associated with a PMIC or a SMIC. For example, a component ID of the target imaging component may be compared to know component IDs. The component ID may correspond to one of the component values discussed above in relation to Table I.

If the target imaging component is the primary manufacturer imaging component, the method 800 may proceed to block 804. At block 804, a request message including a header packet and one or more data packets may be generated. The header packet and the one or more data packets may be generated according to a message protocol. In one embodiment, the header packet may be the same as or similar to the example header packet 400 discussed below in relation to FIG. 4. In some embodiments, the one or more data packets may be the same as or similar to the example data packet 500 discussed below in relation to FIG. 5.

The method 800 continues at block 806 where the request message may be sent to the target imaging component. The target imaging component may be the primary manufacturer imaging component.

If at block 802 it is determined that the target imaging component is not the primary manufacturer imaging component, the method 800 may instead proceed to block 808. At block 808, a communication message including a communication packet may be generated. The communication packet may be generated according to a packet protocol. In one embodiment, the communication packet may be the same as or similar to the example communication packet 300 discussed below in relation to FIG. 3.

The method 800 continues at block 810 where the communication message may be sent to the target imaging component. The target imaging component may be a secondary manufacturer imaging component.

Figure 3:
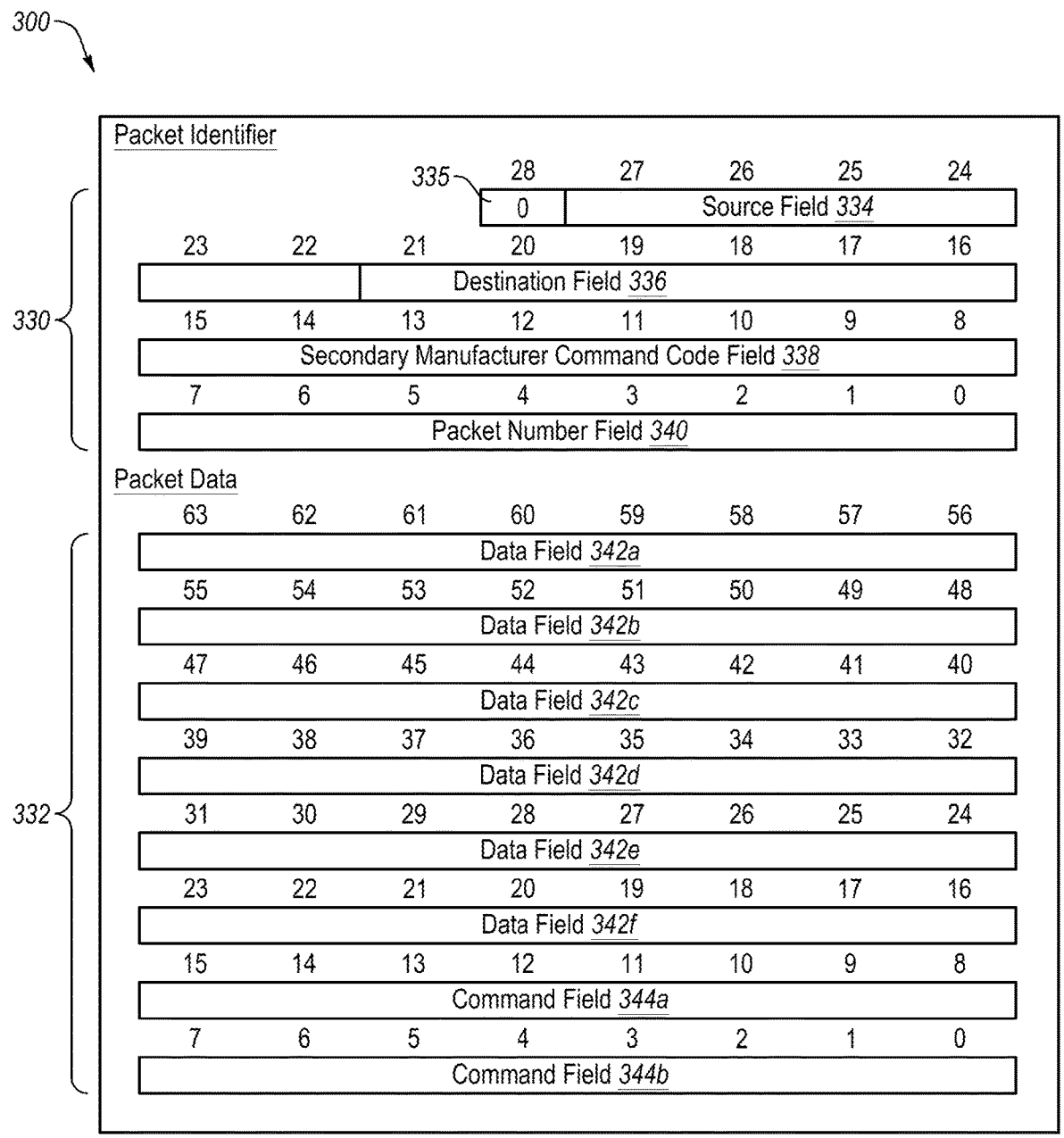
FIG. 3 illustrates an example communication packet sent using an example packet protocol.

FIG. 3 illustrates an example communication packet 300 sent using the packet protocol, according to one or more embodiments disclosed herein. The communication packet 300 may include a communication packet identifier portion 330 and a communication packet data portion 332. In some embodiments, the communication packet 300 may be included in a communication message. For purposes of illustration, the communication packet identifier portion 330 may comprise twenty nine bits, including a reserve field 335, a source field 334, a destination field 336, a SM command code field 338, and a packet number field 340. In one example embodiment, the reserve field 335 may comprise a single bit which may be set to zero. Additionally or alternatively, the reserve field 335 may be set to one.

The source field 334 may comprise six bits and may include a component identification (ID) value associated with the imaging component that generated the communication packet 300. In one non-limiting example, an X-ray imaging system may include six or less imaging components and each bit within the source field 334 may correspond to a single imaging component of the X-ray imaging system (e.g., bitwise decoding). Additionally or alternatively, an X-ray imaging system may include more than six imaging components, in which binary decoding of the value in the source field 334 may be used to determine which imaging component generated the communication packet 300.

For purposes of illustration, the destination field 336 may comprise six bits and may include a component ID value associated with the imaging component that is to receive the communication packet 300. In some embodiments, an X-Ray imaging system may include six or less imaging components and each bit within the destination field 336 may correspond to a single imaging component of the X-ray imaging system. Additionally or alternatively, an X-ray imaging system may include more than six imaging components, in which binary decoding of the value in the destination field 336 may be used to determine which imaging component is to receive the communication packet 300.

Table I illustrates example component ID values of various imaging components that may be included in the communication packet identifier portion 330 (e.g., the source field 334 or the destination field 336) of a communication packet 300 included in messages sent using the packet protocol.

TABLE I

| Component Type | Component ID (Hex Value) | Component ID (Binary Value) |
|---|---|---|
| Host ADB | 0x01 | 000001 |
| Generator ADB | 0x02 | 000010 |
| TAU | 0x04 | 000100 |
| TCU | 0x08 | 001000 |
| Generator | 0x10 | 010000 |
| System Control Unit | 0x20 | 100000 |
| All Imaging Components | 0x3f | 111111 |

For purposes of illustration, the SM command code field 338 may comprise eight bits and may include a SM command code value associated with various commands for the SMIC receiving the communication packet 300. In an example, the SM command code value may have zero value (e.g., 0x00) or a single value. Table II illustrates an example SM command code value that may be included in the SM command code field 338 of the communication packet 300.

TABLE II

| Command Description | SM Command Code Hex Value | Used For |
|---|---|---|
| Generator Communications | 0x00 | May be used for communication packets with secondary manufacturer imaging component ID. First two bytes of a data field may include a subcommand for a particular secondary manufacturer protocol. |

The SM command code value may include a manufacturer specific format (e.g., command code 0x00) for SMICs. For example, a PMIC may transmit a status request to an SMIC such as a temperature request, which may include a value of 0x00 in the SM command code field 338 and a sub command to transmit the temperature of the SMIC. In another example, the SM command code value may have multiple values. For example, each SM command code value may represent a different secondary manufacturer specific protocol. For purposes of illustration, the packet number field 340 may comprise eight bits and may identify a position in a sequence of packets of the communication packet 300. In some embodiments, since the packet protocol may be implemented using single packet communication, a value included in the packet number field 340 may include a value of zero. For purposes of illustration, one example manufacturer specific communication packet data portion 332 may comprise sixty four bits which may include one or more command fields 344a-b and one or more data fields 342a-f, as shown in FIG. 3. The command fields 344a-b may comprise, for example, sixteen bits and may be divided into a first command field 344a and a second command field 344b. The command fields 344a-b may include a command code value for SMICs. In some embodiments, the command fields 344a-b may include an ASCII command value. The data fields 342a-f may include, for example, six bytes and may include data and/or information to be transmitted in the communication packet 300. In some embodiments, the data and/or information to be transmitted in the communication packet 300 may comprise one bit of one of the data fields 342a-f. Additionally or alternatively, the data and/or information to be transmitted in the communication packet 300 may comprise two or more bits of the data fields 342a-f.

For purposes of illustration, the various fields within the communication packet identifier portion 330 and the communication packet data portion 332 are described herein as including a specific number of bytes and/or bits for one example manufacturer specific protocol. However, it will be appreciated that the various fields may include more or less bytes and/or bits than those illustrated or described herein. Different manufacturer specific protocols may have a different configuration of bytes and/or bits and/or number of bytes and/or bits.

Figure 4:
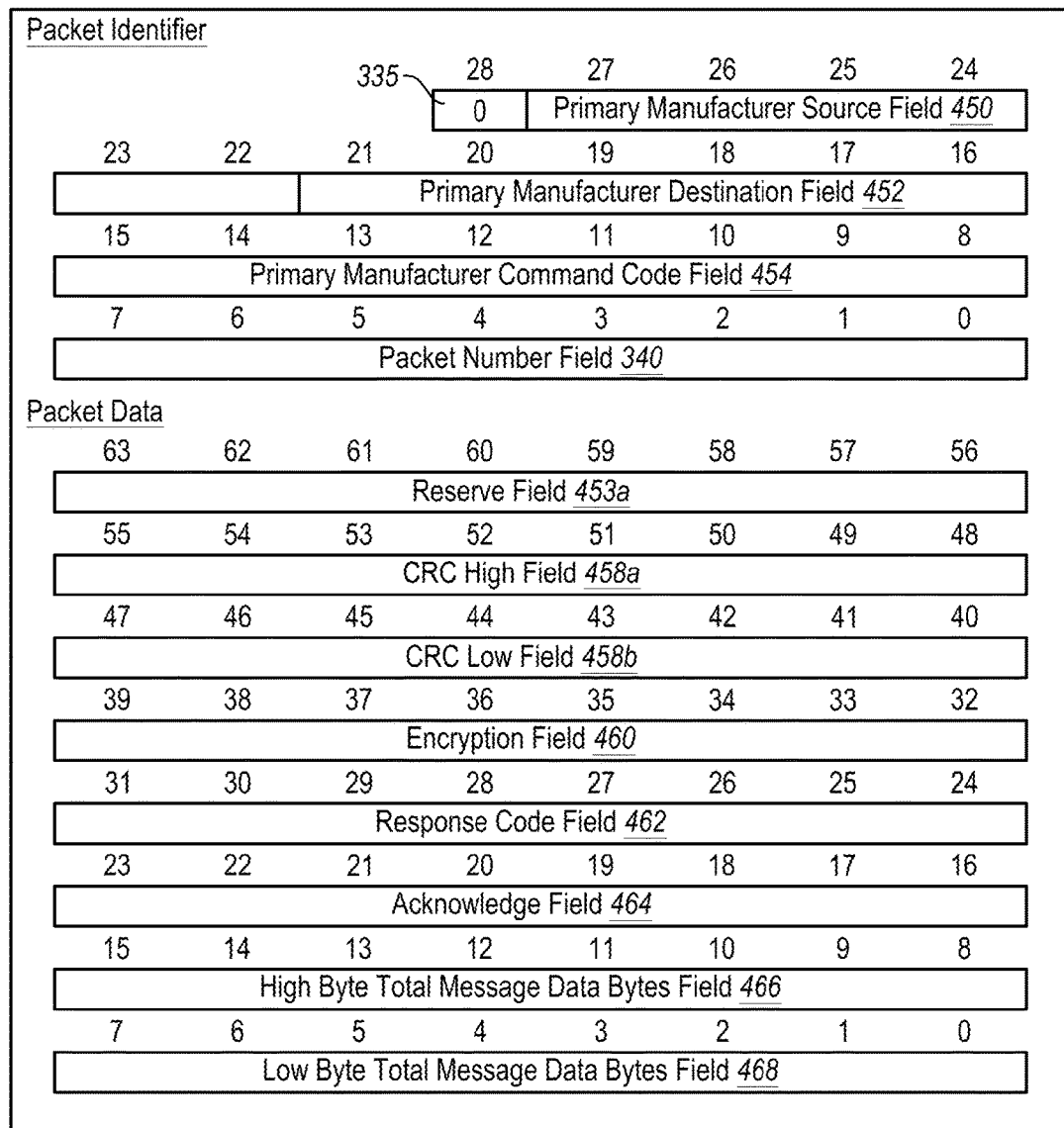
FIG. 4 illustrates an example of a header packet using an example message protocol.

FIG. 4 illustrates an example header packet 400 sent using the message protocol, according to one or more embodiments disclosed herein. The header packet 400 may be included in a request message (e.g., as a request header packet) or a response message (e.g., as a response header packet). The header packet 400 may include a header packet identifier portion 446 and a header packet data portion 448. The header packet identifier portion 446 may comprise twenty nine bits. The header packet identifier portion 446 may include a reserve field 335, a PM source field 450, a PM destination field 452, a PM command code field 454, and a packet number field 340. In one embodiment, the reserve field 335 and the packet number field 340 may be the same as or similar to the example reserve field 335 and the packet number field 340 discussed above in relation to FIG. 3. The PM source field 450, the PM destination field 452, and the PM command code field 454 of the header packet identifier portion 446 (and data packet identifier portion 570 shown in FIG. 5) may be in the same location of the packet as the source field 334, the destination field 336, and the SM command code field 338 of the communication packet identifier portion 330 shown in FIG. 3.

In some embodiment, the reserve field 335 may comprise a single bit which may be set to zero. Additionally or alternatively, the reserve field 335 may be set to one. In some embodiments, a PMIC sending a message via the message protocol may be capable of sending more than eight bytes of data (e.g., multiple packets) per message.

A message sent using the message protocol may include the header packet 400 and one or more data packets, which are discussed in more detail below in relation to FIG. 5. Alternatively, a message sent using the message protocol may include only the header packet 400. The header packet 400 may include information about the message and/or the data and/or information included in the message. For example, the header packet 400 may include information about the data and/or the information to permit a PMIC receiving the message to properly reconstruct the data and/or information. Similarly, the header packet 400 may include data and/or information indicating a source, an encryption technique used, and/or a command structure of the message, which is discussed in more detail below.

The structure of the header packet 400 may support procedures to authenticate PMICs of an X-ray imaging system. For example, implementation of the header packet 400 may provide support for an X-ray tube, smart tube features, and/or predictive failure compensation. In some embodiments, smart tube features may include a history of the type of X-ray shots that have been captured and/or software algorithms that predict tube failure in real time.

The PM source field 450 may include a component ID value associated with the PMIC that generated the header packet 400. The PM source field 450 may comprise six bits and may include a component ID value associated with the PMIC that sent the header packet 400. The component ID value included in the source field 334 may be the same as or similar to the component ID values discussed above in relation to Table I. In some embodiments, an X-ray imaging system may include six or less PMICs and each bit within the source field 334 may correspond to a single PMIC (e.g., bitwise decoding). Additionally or alternatively, an X-ray imaging system may include more than six PMICs, in which binary decoding of the component ID value in the PM source field 450 may be used to determine which PMIC generated the header packet 400.

The PM destination field 452 may include a component ID value associated with the PMIC that is to receive the header packet 400. The PM destination field 452 may comprise, for example, six bits and may include a component ID value associated with the PMIC that is to receive the header packet 400. The component ID value included in the PM destination field 452 may be the same as or similar to the component ID values discussed above in relation to Table I. In some embodiments, an X-ray imaging system may include six or less PMICs and each bit within the PM destination field 452 may correspond to a single PMIC (e.g., bitwise decoding). Additionally or alternatively, an X-ray imaging system may include more than six PMICs, in which binary decoding of the value in the PM destination field 452 may be used to determine which PMIC is to receive the header packet 400.

The PM command code field 454 may include a PM command code value associated with a command for the PMIC which is to receive the header packet 400. The PM command code field 454 may comprise, for purposes of illustration, eight bits. In an example, the PM command code value may have a non-zero value (e.g., 0x01 through 0xFF) or multiple values. Table III illustrates an example PM command code value that may be included in the PM command code field 454 of the header packet 400.

TABLE III

| Command Description | PM Command Code Hex Value | Used For |
|---|---|---|
| Reserved | 0x01 | Reserved. |
| Reserved | 0x02 | Reserved |
| Reserved | 0x03 | Reserved |
| Reserved | 0x04 | Reserved |
| BusInit | 0x05 | May be used at power up. Imaging components may verify they are communicating on the single communication bus. Imaging components may respond to a received BusInit command. |
| Ping | 0x06 | May be used as a watchdog or for trouble shooting. May be used to verify that another imaging component is on the single communication bus. Imaging components may reply to a received ping command. |
| Reset | 0x07 | May be used to request an imaging component reset itself. Imaging components may respond to a received Reset command. |
| WriteLogEntry | 0x08 | May be used to create an entry in a data log. |
| Reserved | 0x09, 0x0A | Reserved |
| RequestErrors | 0x0B | May be used to retrieve an error log. |
| RequestTemperature | 0x0C | May be used to retrieve a temperature reading of an imaging component. |
| RequestDataTable | 0x0D | May be used to retrieve a data table of an imaging component. |
| RequestLogEntry | 0x0E | May be used to read an entry from a data log. |
| Reserved | 0x0F | Reserved. |

TABLE III-continued

| Command Description | PM Command Code Hex Value | Used For |
| --- | --- | --- |
| Authenticate Request | 0x10C | May be used to request an imaging component calculate a digest. May include a challenge sequence. Imaging component may use a shared/secret key to calculate the digest. |
| Reserved | 0x11 | Reserved. |
| Authenticate Success | 0x12 | May be used to indicate the X-ray imaging system has been authenticated. |
| Authenticate Failure | 0x13 | May be used to indicate the X-ray imaging system has failed authentication. |
| Scan Data | 0x14 | May be used to provide exposure data from an X-ray event. |
| Request Scan Log Size | 0x15 | May be used to retrieve a number of entries in the scan log. |
| Request Scan Log Entry | 0x16 | May be used to retrieve a single scan log event. |
| Program SHA | 0x17 | May be used to request an imaging component program an authentication device with a provided secure hash algorithm (SHA) key. |
| Component Memory Write | 0x18 | May be used to request an imaging component write information to component memory. |
| Component Memory Read | 0x19 | May be used to retrieve a field from a componen memory of an imaging component. |
| Display Authentication Log | 0x1A | May be used to request an imaging component send an authentication log to a debug output. |
| Reserved | 0x1B-0xFF | Reserved. |

The PM command code values may include a primary command format (e.g., command codes 0x01 through 0xFF) for PMICs. For example, a PMIC may be replaced and a replacement PMIC may be authenticated prior to operation or communication with other PMICs within an X-ray imaging system. The replacement PMIC may receive a request message from an ADB, such as ADB 720 of FIG. 7, such as an authenticate request PM command code value (e.g., PM command code 0x0C) in the PM command code field 454 of the header packet identifier portion 446 of the header packet 400 included in the request message. The replacement PMIC may send a response message to the ADB including the authenticate request PM command code value (e.g., PM command code 0x0C) in the PM command code field 454 of the header packet 400 of the response message. In these and other embodiments, if the replacement PMIC properly authenticates, the ADB may send a request message to all PMICs within an X-ray imaging system including an authenticate success PM command code value (e.g., PM command code 0x0E) in the PM command code field 454 of the header packet identifier portion 446 of the header packet 400 of the request message. If the replacement PMIC does not properly authenticate, the ADB may send a request message to all PMICs including an authenticate failure PM command code value (e.g., PM command code 0x0F) in the PM command code field 454 of the header packet identifier portion 446 of the header packet 400 of the request message. Therefore, PMICs of an X-ray imaging system may be replaced in a plug-and-play fashion.

Example techniques for authentication by the ADB or other PMICs is further explained in U.S. patent application Ser. No. 15/292,435, which is incorporated in the present disclosure by reference in its entirety.

The packet number field 340 may identify a position in a sequence of packets of the header packet 400. For example, the packet number field 340 in the header packet 400 may be zero (e.g., 0x00) since the header packet 400 is in a first position in the sequence. For purposes of illustration, the header packet data portion 448 may include sixty four bits, including a reserve field 453, one or more cyclic redundancy check (CRC) fields 458a-b (other error-detection code), an encryption field 460, a response code field 462, an acknowledge field 464, a high byte total message data bytes field 466, and a low byte total message data bytes field 468. The reserve field 453 may comprise, for example, eight bits. The eight bits in the reserve field 453 may be used to increase the number of bits in the PM source field 450, the PM destination field 452, the PM command code field 454, and/or the packet number field 340. The CRC fields 458a-b may comprise, for example, sixteen bits which may be divided into a CRC high field 458a and a CRC low field 458b. The CRC fields 458a-b may be used to detect errors in data and/or information to be included in data packets. The CRC fields 458a-b may include a CRC value of the data and/or information to be included in the data packets. For example, a first PMIC may send a request message and may determine the CRC value of the data and/or information as sent and a second PMIC receiving the request message may determine the CRC value of the data and/or information as received and the second PMIC may compare the CRC values to determine whether the CRC values are the same as or similar. The response code field 462 may comprise, for example, eight bits and may identify whether the header packet 400 is associated with a request message (e.g., an original message) or a response message. Table IV illustrates example error codes that may be included in the response code field of the header packet identification portion of a header packet in a response message.

TABLE IV

| Response Code | Value | Description |
| --- | --- | --- |
| CRC_ERROR | 1 | May be used to indicate a CRC error occurred in the request message. |
| DECRYPTION_ERROR | 2 | May be used to indicate an error decrypting data packets of the request message occurred. |
| DATA_WRITE_ERROR | 3 | May be used to indicate an error writing data packets in the response message occurred. |
| UNSUPPORTED_COMMAND | 4 | May be used in development and may indicate a command in the request message is not supported by the PMIC which received it. |
| SECURITY_ERROR | 5 | May be used to indicate a command in the request message was received but cannot be processed because a current security level is insufficient. The current security level may be insufficient due to the PMIC not being authenticated by the PMIC receiving the request prior to sending the request message. |
| BAD_PARAMETER | 6 | May be used to indicate a command in the request message was received which cannot be processed because of a problem with the data included with the command. |
| DATA_READ_ERROR | 7 | May be used to indicate an error reading data packets in the request message occurred. |

Similarly, the acknowledge field 464 may include, for example, eight bits and may include a bus acknowledge code value. For example, the acknowledge field 464 may include a CAN bus reason code value representative of NO_CODE to identify that no errors have occurred. For example, the high byte total message data bytes field 466 may comprise eight bits and the low byte total message data bytes field 468 may comprise eight bits. The high byte total message data bytes field 466 and the low byte total message data bytes field 468 may indicate a number of bytes included in the data and/or information of the data packets.

Again, for ease of discussion and illustration, the various fields within the header packet identifier portion 446 and the header packet data portion 448 are described herein as including a specific number of bytes and/or bits. It will be appreciated that the various fields may include more or less bytes and/or bits than those illustrated or described herein.

Figure 5:
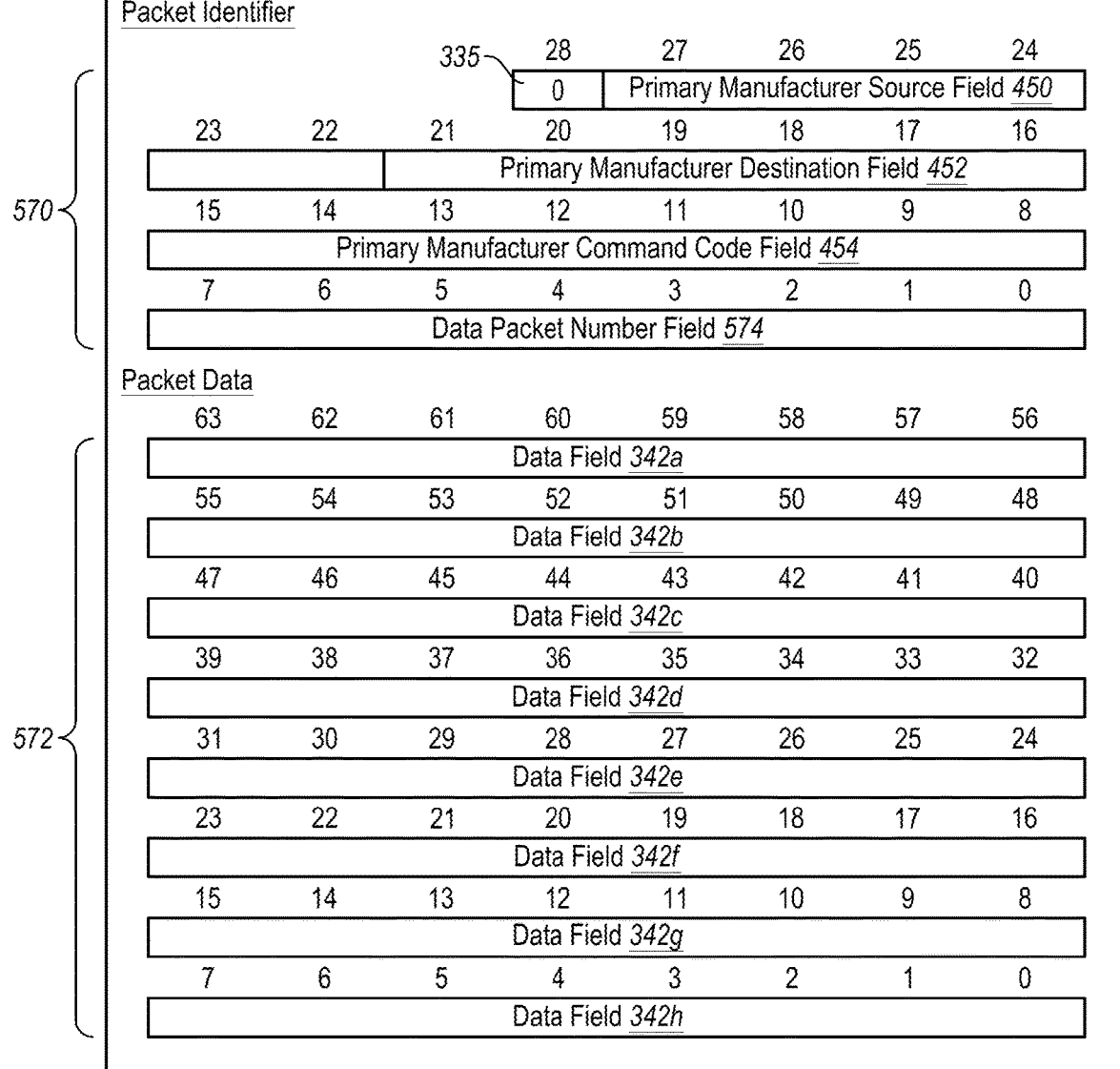
FIG. 5 illustrates another example of a data packet using an example message protocol.

FIG. 5 illustrates an example data packet 500 sent using the message protocol, according to one or more embodiments disclosed herein. The data packet 500 may include a data packet identifier portion 870 and a data packet data portion 872. The data packet identifier portion 870 may comprise twenty nine bits.

In embodiments in which a message includes one or more data packets 500, a header packet, such as the header packet 400 of FIG. 4, may be sent before the data packet 500. In these and other embodiments, the number of data packets 500 included in the message may be based on a command code and may be different for different command codes.

In one example, the data packet identifier portion 870 may include a reserve field 335, a PM source field 450, a PM destination field 452, a PM command code field 454, and a data packet number field 574. The reserve field 335, the PM source field 450, the PM destination field 452, and the PM command code field 454 of the data packet identifier portion 870 may be the same as or similar to the reserve field 335, the PM source field 450, the PM destination field 452, and the PM command code field 454 of the header packet identifier portion 446 discussed above in relation to FIG. 4. The data packet number field 574 may identify the position in the sequence of packets of the data packet 500. In some embodiments, the data packet number field 574 may include a value of one through the number of data packets 500 necessary to send a header packet 400 and the data and/or information in the data packet 500, which may correspond to the size of the data indicated in the header packet 400. The data packet data portion 572 may include the actual data and/or information to be transmitted. Each data packet 500 may include between one and eight bytes of data and/or information. In some embodiments, a message sent via the message protocol may include between one and two hundred fifty six packets.

For purposes of illustration, the data packet data portion 872 may comprise sixty four bits which may include one or more one or more data fields 342a-h, as shown in FIG. 5. The data fields 342a-h may be the same as or similar to the data fields discussed above in relation to FIG. 3. The data fields 342a-h may include, for example, eight bytes and may include data and/or information to be transmitted in the data packet 500. In some embodiments, the data and/or information to be transmitted in the data packet 500 may comprise one bit of one of the data fields 342a-h. Additionally or alternatively, the data and/or information to be transmitted in the data packet 500 may comprise two or more bits of the data fields 342a-h.

As above, the various fields within the data packet identifier portion 870 and the data packet data portion 872 are described as including a specific number of bytes and/or bits. It will be appreciated that the various fields may include more or less bytes and/or bits than those illustrated or described herein.

Figure 9:
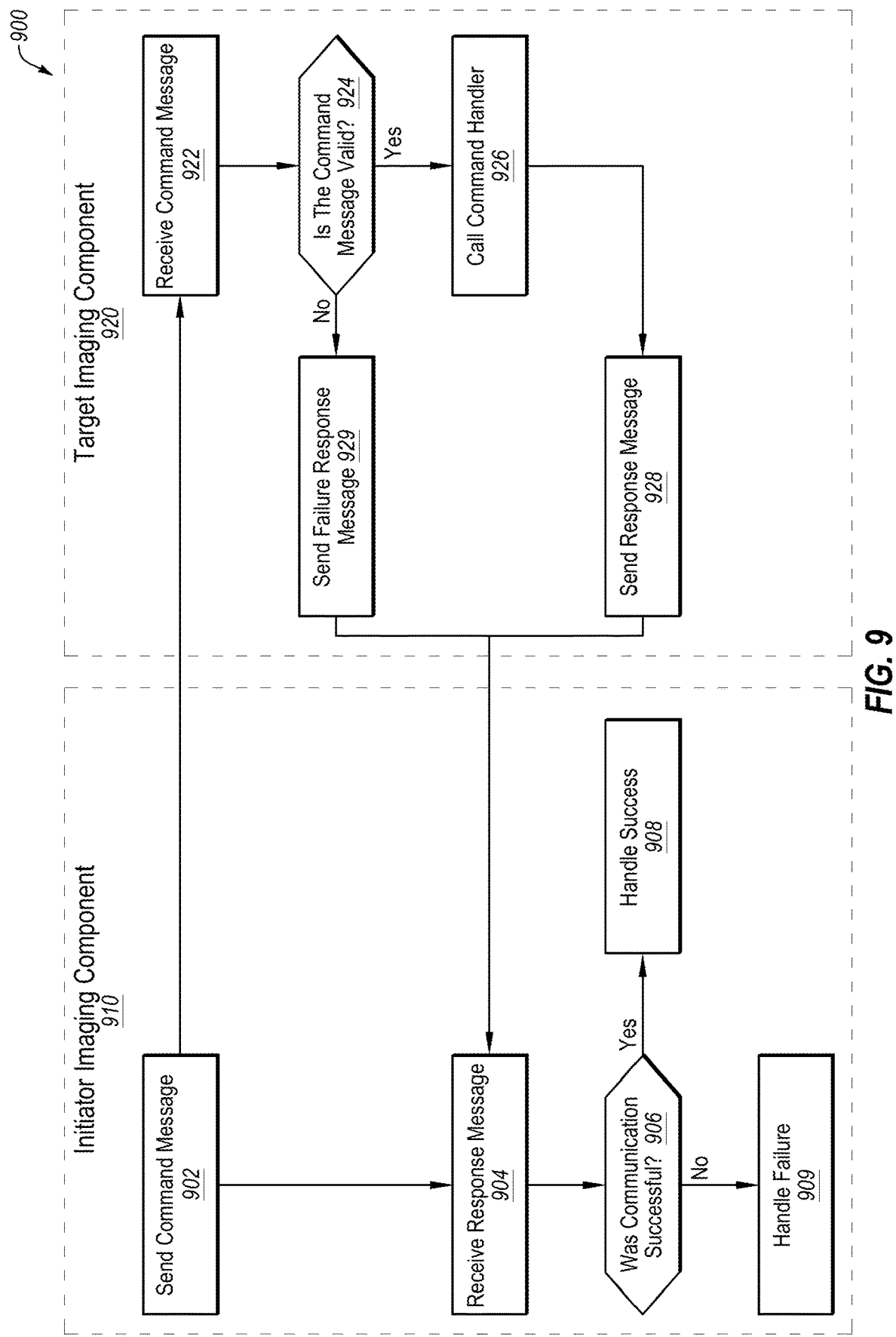
FIG. 9 is a flow chart illustrating an example method for performing a message session between an initiator imaging component and a target imaging component implementing the message protocol.

FIG. 9 is a flow chart illustrating an example method 900 for performing a message session between an initiator imaging component 910 and a target imaging component 920 implementing the message protocol, according to one or more embodiments disclosed herein. The method 900 may be performed by any suitable system, apparatus, or imaging component. For example, the systems 600 and 700 of FIGS. 6 and 7 may direct performance of one or more of the operations associated with the method 900. Although illustrated with discrete blocks, the steps and operations associated with one or more of the blocks of the method 900 may be divided into additional blocks, combined into fewer blocks, or eliminated, depending on the particular implementation. A message session may include transmission of a request message (e.g. an original message) and transmission of a response message.

The method 900 may begin at block 902, in which a command message may be sent by the initiator imaging component 910. The command message may be generated according to a message protocol. The command message may include a header packet and one or more data packets. The command message may include a command for the target imaging component 920 to perform. Additionally or alternatively, the command message may include data that is to be sent to the target imaging component 920.

In some embodiments, the header packet may be the same as or similar to the header packet 400 discussed above in relation to FIG. 4. In these and other embodiments, the data packets may be the same as or similar to the data packet 500 discussed above in relation to FIG. 5. Following block 902, the method 900 may proceed to block 922.

At block 922, the command message may be received by the target imaging component 920. Following block 922, the method may proceed to block 924. At block 924, it may be determined, by the target imaging component 920, whether the command message was valid. In some embodiments, the target imaging component 920 may calculate a CRC value of the command message. The target imaging component 920 may compare the calculated CRC value to a CRC value included in the header packet. In these and other embodiments, the command message may be valid if the calculated CRC value and the CRC value included in the header packet are the same or similar. For example, the target imaging component 920 may compare the calculated CRC value to a CRC value included in a CRC high field and/or a CRC low field in the header packet. The CRC high field and the CRC low field may be the same as or similar to the CRC high field 458a and the CRC low field 458b discussed above in relation to FIG. 4. Responsive to the command message being valid, the method 900 may proceed to block 926.

At block 926, a command handler may be called. In some embodiments, the command handler may determine which command the target imaging component 920 is to perform based on a command value included in a PM command code field in the header packet. The PM command code field may be the same as or similar to the PM command code field 454 discussed above in relation to FIG. 4 and/or FIG. 5. In these and other embodiments, the target imaging component 920 may perform the command. Following block 926, the method 900 may proceed to block 928.

At block 928, a response message may be sent by the target imaging component 920. In some embodiments, the response message may be generated according to the message protocol. Additionally, the response message may include a header packet and one or more data packets. Alternatively, the response message may include a header packet only.

In some embodiments, the response message may indicate that the target imaging component 920 performed the command indicated in the PM command code field. In other embodiments, the response message may include data to be sent to the initiator imaging component 910.

In some embodiments, one or more fields in the header packet may be set to indicate an error did not occur during transmission and/or receipt of the command message. For example, an acknowledge field may be set to a value representative of the code NO_CODE (to indicate receipt of the command message without an error). The acknowledge field may be the same as or similar to the acknowledge field 464 discussed above in relation to FIG. 4. Following block 928, the method 900 may proceed to block 904.

Responsive to the command message not being valid, the method 900 may proceed to block 929. At block 929, a failure response message may be sent by the target imaging component 920. In some embodiments, the failure response message may be generated according to the message protocol. Additionally, the failure response message may include a header packet and one or more data packets. Alternatively, the failure response message may include a header packet only.

In some embodiments, one or more fields in the header packet may be set to indicate an error occurred during transmission and/or receipt of the command message. For example, the acknowledge field may be set to a value representative of the code ACK ERROR (to indicate acknowledgment of the request message with an error). Following block 929, the method 900 may proceed to block 904.

At block 904, the failure response message or the response message may be received by the target imaging component 920. Following block 904, the method may proceed to block 906.

At block 906, it may be determined, by the initiator imaging component 910, whether communication was successful. In some embodiments, the initiator may calculate a CRC value of the response message or the failure response message. If the calculated CRC value of the response message or the failure response message is the same as or similar to a CRC value included in the header packet of the response message or the failure response message, the initiator imaging component 910 may determine an error did not occur during transmission and/or receipt of the response message or the failure response message.

Additionally, the initiator imaging component may determine if one or more fields in the header packet of the response message or the failure response message are set to indicate an error occurred during transmission and/or receipt of the command message. Responsive to the communication being successful, the method 900 may proceed to block 908. At block 908, the success may be handled by the initiator imaging component 910. For example, the initiator imaging component 910 may update a status of the target imaging component 920 as having performed the command in the command message in a data base or the initiator imaging component 910 may perform some other function based on the communication being successful.

Responsive to the communication not being successful, the method 900 may proceed to 909. At block 909, the failure may be handled. For example, the initiator imaging component 910 may start a new message session by sending another command message including the same or a similar header packet and/or one or more data packets or the initiator imaging component 910 may perform some other function based on the communication not being successful.

Figure 10:
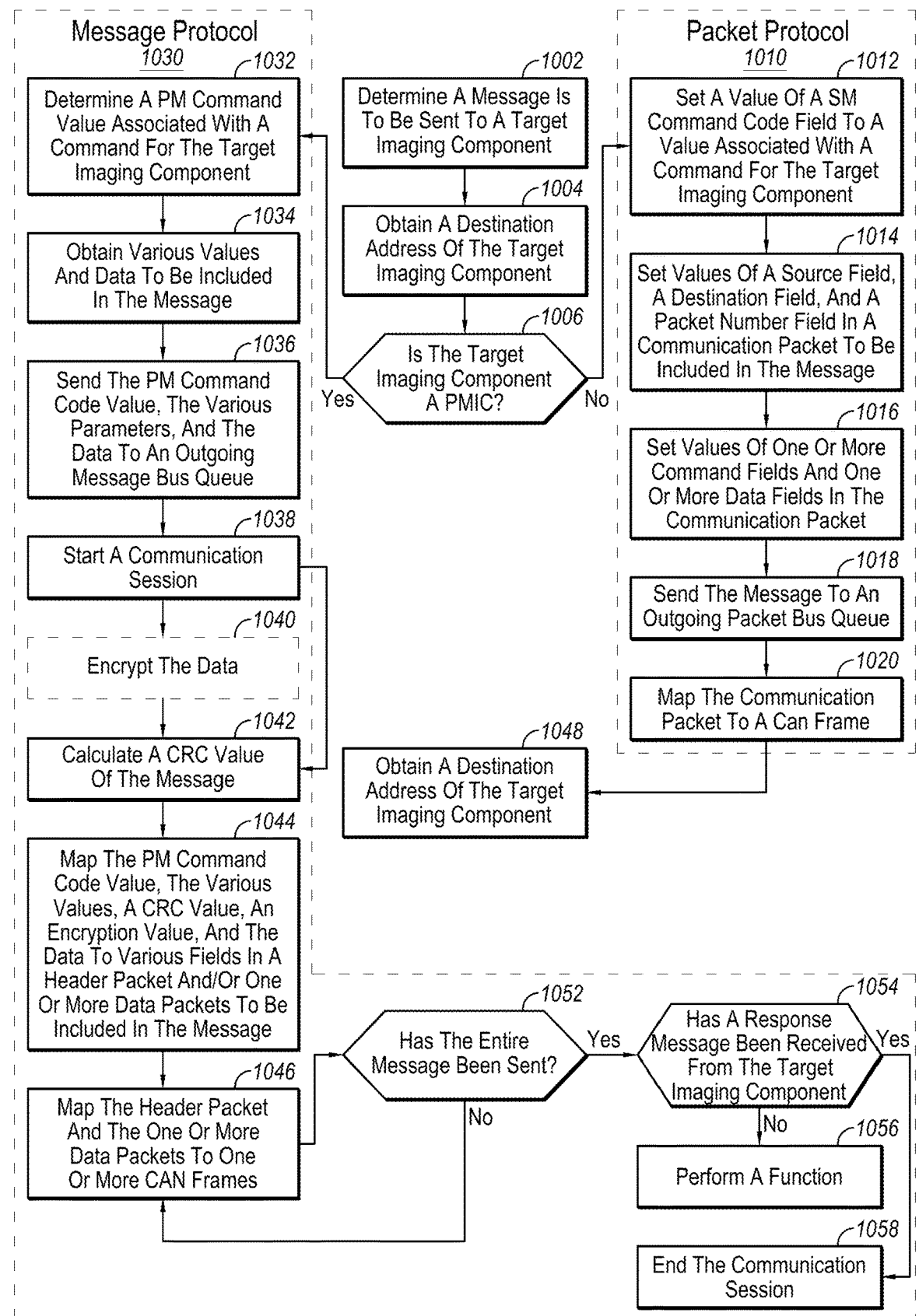
FIG. 10 is a flow chart illustrating an example method for generating and sending a message using a flexible communication protocol.

FIG. 10 is a flow chart illustrating an example method 1000 for generating and sending a message using a flexible communication protocol, according to one or more embodiments disclosed herein. The method 1000 may be performed by any suitable system, apparatus, or imaging component. For example, the systems 600 and 700 of FIGS. 6 and 7 may direct performance of one or more of the operations associated with the method 1000. Although illustrated with discrete blocks, the steps and operations associated with one or more of the blocks of the method 1000 may be divided into additional blocks, combined into fewer blocks, or eliminated, depending on the particular implementation. Communicating using the flexible communication protocol may include generating messages according to a message protocol 1030 and/or a packet protocol 1010.

The method 1000 may begin at block 1002, in which the message to be sent to a target imaging component may be determined. In some embodiments, the message to be sent may be a communication message that is to be sent to a SMIC. Alternatively, the message to be sent may be a request message or a response message to be sent to a PMIC. Following block 1002, the method 1000 may proceed to block 1004. At block 1004, a destination address of the target imaging component may be obtained. Following block 1004, the method 1000 may proceed to block 1006.

At block 1006, it may be determined whether the target imaging component is a PMIC. For example, it may be determined whether the destination address is included in a list of PMIC addresses or a list of SMIC addresses. For example, the destination address may correspond to one of the component values discussed above in relation to Table I.

In response to determining that the target imaging component is not a PMIC, the method 1000 may proceed to block 1012. In some embodiments, the operations of blocks 1012, 1014, 1016, 1018, and 1020 may be performed according to the packet protocol 1010. The packet protocol 1010 may be the same as or similar to the packet protocol discussed elsewhere in the present disclosure.

At block 1012, a value of a SM command code field may be set to a value associated with a command for the target imaging component. The value set in the SM command code field may be representative of a command for the target imaging component to perform. Additionally, the value set in the SM command code field may be a SM command code value. The SM command code value may include one of the SM command code values discussed above in relation to Table II.

In some embodiments, the SM command code field may be the same as or similar to the SM command code field 338 discussed above in relation to FIG. 3. Following block 1012, the method 1000 may proceed to block 1014.

At block 1014, values of a source field, a destination field, and a packet number field in a communication packet to be included in the message may be set. The value set in the source field may be representative of an address of an initiator imaging component (e.g., the imaging component that is generating the communication packet). The value set in the destination field may be representative of the address of the target imaging component. Additionally, the value set in the packet number field may be representative of a position in a sequence of packets of the communication packet. For example, in some embodiments, the communication packet may be implemented using single packet communication. In these and other embodiments, the value in the packet number field may include a value of zero.

In some embodiments, the source field, the destination field, and the packet number field may be the same as the source field 334, the destination field 336, and the packet number field 340 discussed above in relation to FIG. 3, respectively. Following block 1014, the method 1000 may proceed to block 1016.

At block 1016, values of one or more command fields and one or more data fields in the communication packet may be set. The values in the data fields may be representative of data to be sent to the target (or receiving) imaging component. The values in the command fields may include a command code value for SMICs.

In some embodiments, the command fields and the data fields may be the same as or similar to the command fields 344a-344b and the data fields 342a-342f discussed above in relation to FIG. 3, respectively. Following block 1016, the method 1000 may proceed to block 1018.

At block 1018, the message may be sent to an outgoing packet bus queue. Following block 1018, the method 1000 may proceed to block 1020. At block 1020, the communication packet may be mapped to a CAN frame. A CAN frame may include one hundred twenty eight bits. The communication packet may include ninety three bits. Each bit in the communication packet may be mapped to a bit in the CAN frame. Following block 1020, the method 1000 may proceed to block 1048.

In response to determining that the target imaging component is a PMIC, the method 1000 may proceed to block 1032. In some embodiments, the operations of blocks 1032, 1034, 1036, 1038, 1040, 1042, 1044, 1046, 1052, 1054, 1056, and 1058 may be performed according to the message protocol 1030. The message protocol 1030 may be the same as or similar to the message protocol discussed elsewhere in the present disclosure.

At block 1032, a PM command value associated with a command for the target imaging component may be determined. For example, the PM command value may include one or more of the PM command code values discussed above in relation to Table III. Following block 1032, the method 1000 may proceed to block 1034.

At block 1034, various values and data to be included in the message may be obtained. For example, values corresponding to a PM source address, a PM destination address, and a packet number may be obtained. As another example, values corresponding to a response code, an acknowledge code, a high byte total message data bytes value, and/or a low byte total message data bytes value may be obtained. Additionally, the data to be included in the message may be obtained. Following block 1034, the method 1000 may proceed to block 1036.

At block 1036, the PM command code value, the various values, and the data may be sent to an outgoing message bus queue. Following block 1036, the method 1000 may proceed to block 1038.

At block 1038, a communication session may be started. In some embodiments, a communication session may include one or more request messages and one or more response messages being sent between two or more PMICs. In some embodiments, when the data is to be encrypted, the method 1000 may proceed to block 1040. In other embodiments, when the data is not to be encrypted, the method 1000 may proceed to block 1042.

At block 1040, the data may be encrypted. In some embodiments, the data may be encrypted using any appropriate encryption method. In these and other embodiments, an encryption value may be determined. The encryption value may indicate whether the message and/or data is encrypted. Additionally, the encryption value may indicate the method of encryption that was used. Following block 1040, the method 1000 may proceed to block 1042.

At block 1042, a CRC value of the message may be calculated. In some embodiments, the CRC value may be representative of a size of the entire message. In other embodiments, the CRC value may be representative of a size of the data only. The CAN frame may also use a CRC field, which is used for the size of just the frame. Following block 1042, the method 1000 may proceed to block 1044.

At block 1044, the PM command code value, the various values, the CRC value, the encryption value, and the data may be mapped to various fields in a header packet and/or one or more data packets to be included in the message. The header packet may be the same as or similar to the header packet 400 discussed above in relation to FIG. 4. Additionally, the one or more data packets may be the same as or similar to the data packet 500 discussed above in relation to FIG. 5.

Furthermore, the various fields in the header packet and/or the one or more data packets may be included in a header packet identifier portion, a header packet data portion, a data packet identifier portion, and/or a data packet data portion. In some embodiments, the header packet identifier portion, the header packet data portion, the data packet identifier portion, and the data packet data portion may be the same as or similar to the header packet identifier portion 446, the header packet data portion 448, the data packet identifier portion 870, and the data packet data portion 872 discussed above in relation to FIG. 4 and/or FIG. 5, respectively.

In some embodiments, the values corresponding to the PM source address may be mapped to a PM source field, the PM destination address may be mapped to a PM destination field, and the packet number may be mapped to packet number field or a data packet number field.

The value set in the PM source field may be representative of an address of the initiator imaging component (e.g., the imaging component that is generating the header packet and the one or more data packets). The value set in the PM destination field may be representative of the address of the target imaging component. Additionally, the value set in the packet number field and/or the data packet number field may be representative of a position in a sequence of packets of the header packet and the one or more data packets.

In these and other embodiments, the PM source field, the PM destination field, the packet number field, and the data packet number field may be the same as or similar to the PM source field 450, the PM destination field 452, the packet number field 340, and the data packet number field 574 discussed above in relation to FIG. 4 and/or FIG. 5, respectively.

Additionally, the PM command code value may be mapped to a PM command code field, the CRC value may be mapped to a CRC high field and/or a CRC low field, the encryption value may be mapped to an encryption field, the response code may be mapped to a response code field, the acknowledge code may be mapped to an acknowledge field, the high byte total message data bytes value may be mapped to a high byte total message data bytes field, and/or the low byte total message data bytes value may be mapped to a low byte total message data bytes field.

The value set in the response code field may indicate whether the message is a response message or a request message. For example, the response code field may be set to a value representative of the code ACK or NOT_A_RESPONSE. Alternatively, if the response code field is set to a value representative of NOT_A_RESPONSE, the message may be a request message. In some embodiments, the value set in the acknowledge field may indicate whether the message is a response message and if any errors have occurred. For example, the acknowledge field may be set to a value representative of the code NO_CODE, which may indicate that the message is a response message and no errors have occurred. Additionally, the value set in the high byte total message data bytes field and/or the low byte total message data bytes field may indicate a number of bytes included in the data and/or information of the data packets. Furthermore, the data may be mapped to one or more data fields. In some embodiments, the one or more data field may be the same as or similar to the data fields 342a-342h discussed above in relation to FIG. 5.

In some embodiments, the PM command code field, the CRC high field, the CRC low field, and the encryption field may be the same as or similar to the PM command code field 454, the CRC high field 458a, the CRC low field 458b, and the encryption field 460 discussed above in relation to FIG. 4 and/or FIG. 5, respectively. Additionally, the response code field, the acknowledge field, the high byte total message data bytes field, and the low byte total message data bytes field may be the same as or similar to the acknowledge field 464, the high byte total message data bytes field 466, and the low byte total message data bytes field 468 discussed above in relation to FIG. 4, respectively. Following block 1044, the method 1000 may proceed to block 1046.

At block 1046, the header packet and the one or more data packets may be mapped to one or more CAN frames. Each CAN frame may include one hundred twenty eight bits. The header packet and each data packet may include ninety three bits. Each bit in the header packet and/or the one or more data packets may be mapped to a bit in a CAN frame. Following block 1046, the method 1000 may proceed to block 1048 and 1052.

At block 1048, a packet of the message may be sent on a flexible communication bus. In some embodiments, the message may include the communication packet and the message may be a communication message sent to a SMIC. In other embodiments, the message may include the header packet and the one or more data packets. Alternatively, the message may include the header packet only. Additionally, the message may be a request message or a response message sent to a PMIC. In some embodiments, the flexible communication bus may be the same as or similar to the flexible communication bus 764 discussed above in relation to FIG. 4

At block 1052, it may be determined whether the entire message has been sent. In some embodiments, the packet number value in the packet number field may be used to determine whether the entire message has been sent. For example, the message may include three data packets and the data packet most recently sent may include a packet number value in the packet number field representative of three data packets and one header packet being sent.

In response to determining that the entire message has not been sent, the method 1000 may proceed to block 1046. The method 1000 may repeat the operations of blocks 1046 and 1052 until the entire message has been sent. In response to determining that the entire message has been sent, the method 1000 may proceed to block 1054.

At block 1054, it may be determined whether a response message has been received from the target imaging component. In response to a response message being received, the method may proceed to block 1058. At block 1058, the communication session may end. In response to a response message not being received, the method may proceed to block 1056. At block 1056, a function may be performed. For example, the function can be a call to an error handler. The error handler may resend the message or send a message to another imaging component, such as a host device or host ADB.

Figure 11:
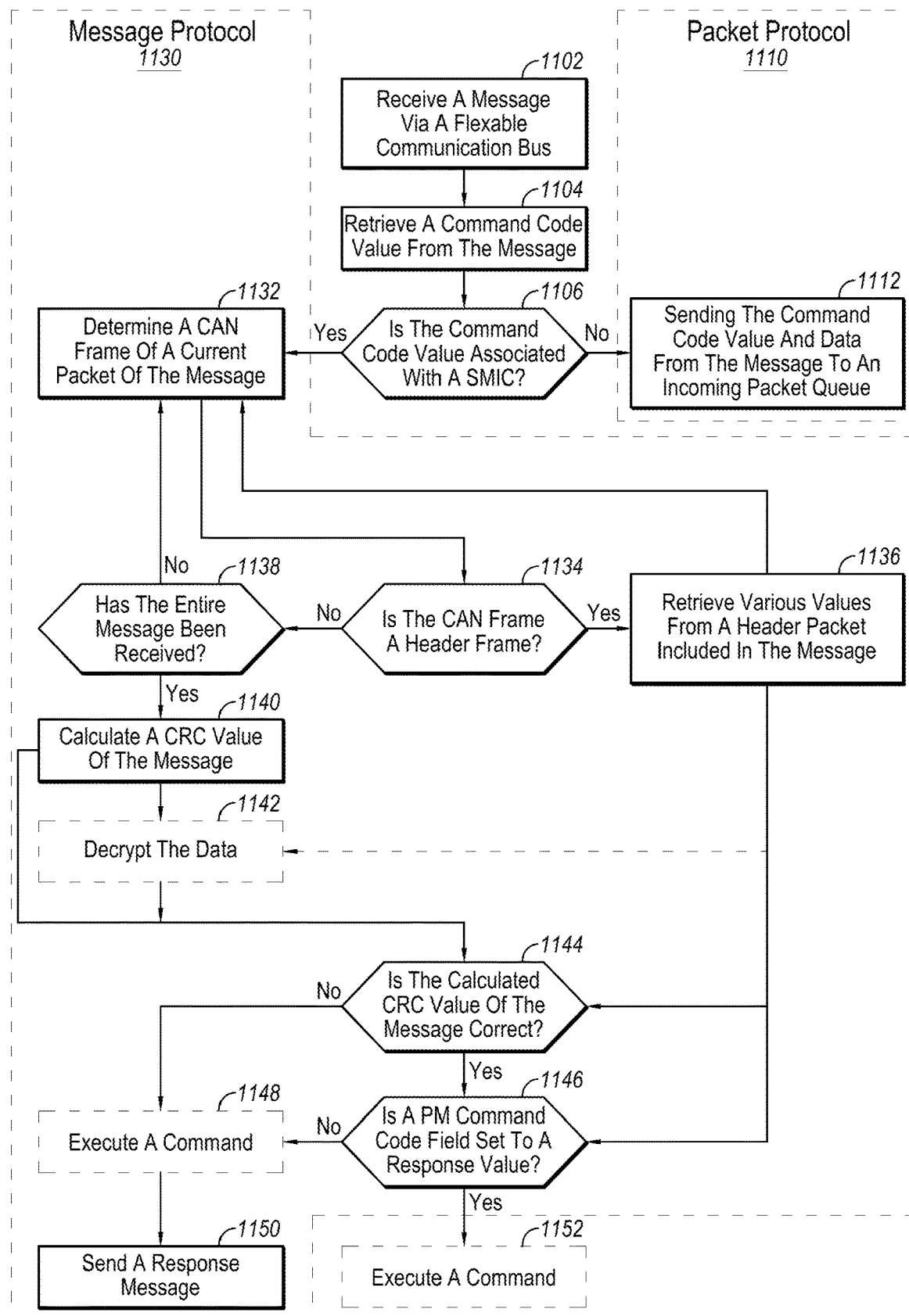
FIG. 11 is a flow chart illustrating an example method for receiving a message according to a flexible communication protocol.

FIG. 11 is a flow chart illustrating an example method 1100 for receiving a message according to a flexible communication protocol, according to one or more embodiments disclosed herein. The method 1100 may be performed by any suitable system, apparatus, or imaging component. For example, the systems 600 and 700 of FIGS. 6 and 7 may direct performance of one or more of the operations associated with the method 1100. Although illustrated with discrete blocks, the steps and operations associated with one or more of the blocks of the method 1100 may be divided into additional blocks, combined into fewer blocks, or eliminated, depending on the particular implementation. Communicating using the flexible communication protocol may include determining whether the message has been generated according to a message protocol 1130 and/or a packet protocol 1110.

The method 1100 may begin at block 1102, in which the message may be received via a flexible communication bus. In some embodiments, the message may include a communication packet and a target imaging component may include a SMIC. In other embodiments, the message may include a header packet and one or more data packets and the target imaging component may include a PMIC. Alternatively, the message may include the header packet only. In one embodiment, the flexible communication bus may be the same as or similar to the flexible communication bus 764 discussed above in relation to FIG. 4. Following block 1102, the method 1100 may proceed to block 1104.

At block 1104, a command code value may be retrieved from the message. In some embodiments, the command code value may be a SM command code value included in a SM command code field in the communication packet. In these and other embodiments, the SM command code field may be the same as or similar to the SM command code field 338 discussed above in relation to FIG. 3. In other embodiments, the command code value may be a PM command code value included in a PM command code field in the header packet or a data packet. In these and other embodiments, the PM command code field may be the same as or similar to the PM command code field 454 discussed above in relation to FIG. 4 and/or FIG. 5. Following block 1104, the method 1100 may proceed to block 1106.

At block 1106, it may be determined whether the command code value is associated with a SMIC. For example, the command code value in the message may be compared to the PM command code values and the SM command code value discussed above in relation to Table II and Table III. If the command code value in the message is the same as or similar to one of the PM command code values in Table III, the command code value may not be associated with a SMIC. If the command code value in the message is the same as or similar to the SM command code value in Table II, the command code value may be associated with a SMIC.

In response to determining that the command code value is associated with a SMIC, the method 1100 may proceed to block 1112. In some embodiments, the operations of block 1112 may be performed according to the packet protocol 1110. The packet protocol 1010 may be the same as or similar to the packet protocol discussed elsewhere in the present disclosure. At block 1112, the command code value and data from the message may be sent to an incoming packet queue.

In response to determining that the command code value is not associated with a SMIC, the method 1100 may proceed to block 1132. In some embodiments, the operations of blocks 1132, 1134, 1136, 1138, 1140, 1142, 1144, 1146, 1148, 1150, and 1152 may be performed according to the message protocol 1130. The message protocol 1130 may be the same as or similar to the message protocol discussed elsewhere in the present disclosure.

At block 1132, a CAN frame of a current packet of the message may be determined. A CAN frame may include one hundred twenty eight bits and each packet may include ninety three bits. In some embodiments, one packet may fit per CAN frame. Following block 1132, the method 1100 may proceed to block 1134.

At block 1134, it may be determined whether the CAN frame is a header frame. For example, it may be determined whether the CAN frame corresponds to a header packet or a data packet of the message. If the CAN frame corresponds to a header packet of the message, the CAN frame may be a header frame. If the CAN frame corresponds to a data packet of the message, the CAN frame may not be a header frame. In some embodiments, the header packet and the data packets may be the same as or similar to the header packet 400 and the data packet 500 discussed above in relation to FIG. 4 and FIG. 5, respectively.

In response to determining that the CAN frame is a header frame, the method 1100 may proceed to block 1136. At block 1136, various values may be retrieved from the header packet included in the message. In some embodiments, the various values may include an encryption value, a CRC value, and/or a PM command code value. In some embodiments, the encryption value may be included in an encryption field, the CRC value may be included in a CRC high field and/or a CRC low field, and the PM command code value may be included in a PM command code field. In some embodiments, the PM command code field, the CRC high field, the CRC low field, and the encryption field may be the same as or similar to the PM command code field 454, the CRC high field 458a, the CRC low field 458b, and the encryption field 460 discussed above in relation to FIG. 4 and/or FIG. 5, respectively.

In some embodiments, the various values retrieved from the header packet included in the message may be used to determine whether an error occurred during transmission and/or receipt of the message or to decrypt the message. For example, the encryption value may be used in the operations of block 1142 as discussed below. As another example, the CRC value may be used in the operations of block 1144 as discussed below. As yet another example, the PM command code value may be used in the operations of block 1146 as discussed below. Following block 1136, the method 1100 may return to block 1132. The operations of blocks 1132 and 1134 may be repeated until a CAN frame of the current packet of the message is not a header frame.

In response to determining that the CAN frame of the current packet of the message is not a header frame, the method 1100 may proceed to block 1138. At block 1138, it may be determined whether the entire message has been received. For example, the message may include a header packet and two data packets and the data packet most recently received may include a packet number value in the packet number field representative of two data packets and one header packet being received.

In response to determining that the entire message has not been received, the method 1100 may return to block 1132. The method 1100 may repeat the operations of blocks 1132, 1134, 1136, and 1138 until the entire message has been received. In response to determining that the entire message has been received, the method 1100 may proceed to block 1140.

At block 1140, a CRC value of the message may be calculated. The CRC value may be representative of a size of the message. In some embodiments, the CRC value may be representative of the size of the entire message. In other embodiments, the CRC value may be representative of a size of the data only.

In some embodiments, when the data included in the message is encrypted (e.g., the encryption value in the encryption field retrieved during the operations of block 1136 indicates the data is encrypted and which encryption technique was used), the method 1100 may proceed to block 1142. In other embodiments, when the data included in the message is not encrypted (e.g., the encryption value in the encryption field retrieved during the operations of block 1136 indicates the data is not encrypted), the method 1100 may proceed to block 1144.

At block 1142, the data may be decrypted. The data may be decrypted using any appropriate decryption technique. Following block 1142, the method 1100 may proceed to block 1144.

At block 1144, it may be determined whether the calculated CRC value of the message is correct. In some embodiments, the calculated CRC value may be compared to the CRC value retrieved during the operations of block 1136. If the calculated CRC value is the same as or similar to the CRC value retrieved during the operations of block 1136, no errors may have occurred during transmission and/or receipt of the message. Alternatively, if the calculated CRC value is not the same as or similar to the CRC value retrieved during the operations of block 1136, errors may have occurred during transmission and/or receipt of the message.

In response to the calculated CRC value being correct, the method 1100 may proceed to block 1146. At block 1146 it may be determined whether a PM command code field is set to a response value. For example, the PM command value in the PM command code field may include one or more of the PM command code values discussed above in relation to Table III.

In response to the PM command code field not being set to a response value, the method 1100 may proceed to block 1148. At block 1148, a command may be executed. The command may correspond to the command included in the message. Following block 1148, the method 1100 may proceed to block 1150. Additionally, in response to the calculated CRC value not being correct, the method 1100 may proceed to block 1150.

At block 1150, a response message may be sent. The response message may be generated according to the message protocol 1130. Additionally, the response message may be generated according to the method 1000 discussed above in relation to FIG. 10.

In response to the PM command code field being set to a response value, the method 1100 may proceed to block 1152. At block 1152, a function may be performed.

Figure 12:
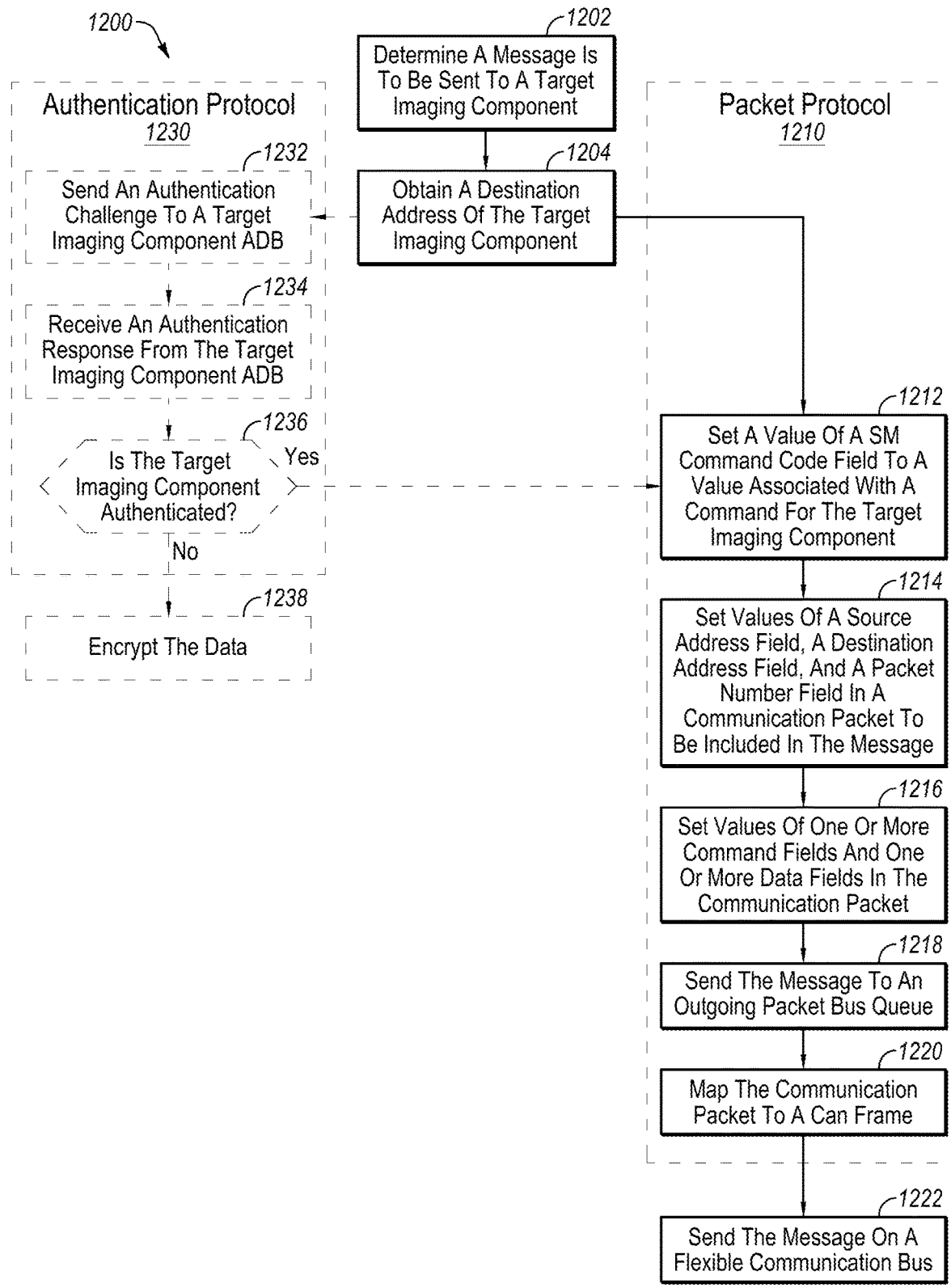
FIG. 12 is a flow chart illustrating an example method for sending a message using a packet protocol and authenticating a secondary manufacturer imaging component (SMIC) according to an authentication protocol.

FIG. 12 is a flow chart illustrating an example method 1200 for sending a message using a packet protocol 1210 and authenticating a SMIC according to an authentication protocol 1230, according to one or more embodiments disclosed herein. In some examples, the authentication protocol can use the message protocol as described above. The method 1200 may be performed by any suitable system, apparatus, or imaging component. For example, the systems 600 and 700 of FIGS. 6 and 7 may direct performance of one or more of the operations associated with the method 1200. Although illustrated with discrete blocks, the steps and operations associated with one or more of the blocks of the method 1200 may be divided into additional blocks, combined into fewer blocks, or eliminated, depending on the particular implementation. Communicating using the packet protocol may include generating messages according to the packet protocol.

The method 1200 may begin at block 1202, in which the message to be sent to a target imaging component may be determined. In some embodiments, the message to be sent may be a communication message that is to be sent to a SMIC or by a SMIC. Following block 1202, the method 1200 may proceed to block 1204.

At block 1204, a destination address of the target imaging component may be obtained. In some embodiments, the target imaging component may be authenticated, when the target imaging component is to be authenticated, the method 1200 may proceed to block 1232. In some embodiments, the operations of blocks 1232, 1234, and 1236 may be performed according to the authentication protocol 1230. The authentication protocol 1230 may be the same as or similar to the message protocol discussed elsewhere in the present disclosure.

In other embodiments, when the target imaging component is not to be authenticated, the method 1200 may proceed to block 1212. In some embodiments, the operations of blocks 1212, 1214, 1216, 1218, and 1220 may be performed according to the packet protocol 1210. The packet protocol 1210 may be the same as or similar to the packet protocol discussed elsewhere in the present disclosure.

At block 1212, a value of a SM command code field may be set to a value associated with a command for the target imaging component. The value set in the SM command code field may be representative of a command for the target imaging component to perform. Additionally, the value set in the SM command code field may be a SM command code value. The SM command code value may include one of the SM command code values discussed above in relation to Table II.

In some embodiments, the SM command code field may be the same as or similar to the SM command code field 338 discussed above in relation to FIG. 3. Following block 1212, the method 1200 may proceed to block 1214.

At block 1214, values of a source field, a destination field, and a packet number field in a communication packet to be included in the message may be set. The value set in the source field may be representative of an address of an initiator imaging component (e.g., the imaging component that is generating the communication packet). The value set in the destination field may be representative of the address of the target imaging component. Additionally, the value set in the packet number field may be representative of a position in a sequence of packets of the communication packet. For example, in some embodiments, the communication packet may be implemented using single packet communication. In these and other embodiments, the value in the packet number field may include a value of zero.

In some embodiments, the source field, the destination field, and the packet number field may be the same as the source field 334, the destination field 336, and the packet number field 340 discussed above in relation to FIG. 3, respectively. Following block 1214, the method 1200 may proceed to block 1216.

At block 1216, values of one or more command fields and one or more data fields in the communication packet may be set. The values in the data fields may be representative of data to be sent to the target imaging component. The values in the command fields may include a command code value for SMICs In some embodiments, the command fields and the data fields may be the same as or similar to the command fields 344a-344b and the data fields 342a-342f discussed above in relation to FIG. 3, respectively. Following block 1216, the method 1200 may proceed to block 1218.

At block 1218, the message may be sent to an outgoing packet bus queue. Following block 1218, the method 1200 may proceed to block 1220. At block 1220, the communication packet may be mapped to a CAN frame. A CAN frame may include one hundred twenty eight bits. The communication packet may include ninety three bits. Each bit in the communication packet may be mapped to a bit in the CAN frame. Following block 1220, the method 1200 may proceed to block 1222.

At block 1222, the message may be sent on a flexible communication bus. In some embodiments, the message may include the communication packet and the message may be sent to a SMIC. In one embodiment, the flexible communication bus may be the same as or similar to the flexible communication bus 764 discussed above in relation to FIG. 4.

At block 1232, an authentication challenge may be sent to the receiving (or target) imaging component ADB. The authentication challenge may be generated according to the authentication protocol 1230. In some embodiments, an initiating imaging component may be a PMIC and the receiving (or target) imaging component ADB may also be a PMIC. The target imaging component and the initiator imaging component ADB may communicate via the authentication protocol/message protocol. Additionally, the authentication challenge may be included in a request message that includes a PM command code value associated with authentication of a SMIC (e.g., PM command code 0x0C) in a PM command code field of a header packet included in the request message.

In some embodiments, the header packet may be the same as or similar to the header packet 400 discussed above in relation to FIG. 4. Additionally, the PM command code field may be the same as or similar to the PM command code field 454 discussed above in relation to FIG. 4. In other embodiments, the target imaging component ADB may include the ADB 720 discussed above in relation to FIG. 4. Following block 1232, the method 1200 may proceed to block 1234.

At block 1234, an authentication response from the target imaging component ADB may be received. The authentication response may be generated according to the authentication protocol 1230. The target imaging component ADB may send a response message to the receiving imaging component including a PM command code value associated with an authentication of the SMIC in the PM command code field of the header packet of the response message.

Following block 1234, the method 1200 may proceed to block 1236. At block 1236, it may be determined whether the target imaging component is authenticated. For example, it may be determined whether the response message included the PM command code value is associated with an authentication of the target imaging component.

In response to the target imaging component being authenticated, the method 1200 may proceed to block 1212. In response to the target imaging component not being authenticated, the method 1200 may proceed to block 1238. At block 1238, a function may be performed.

Figure 13:
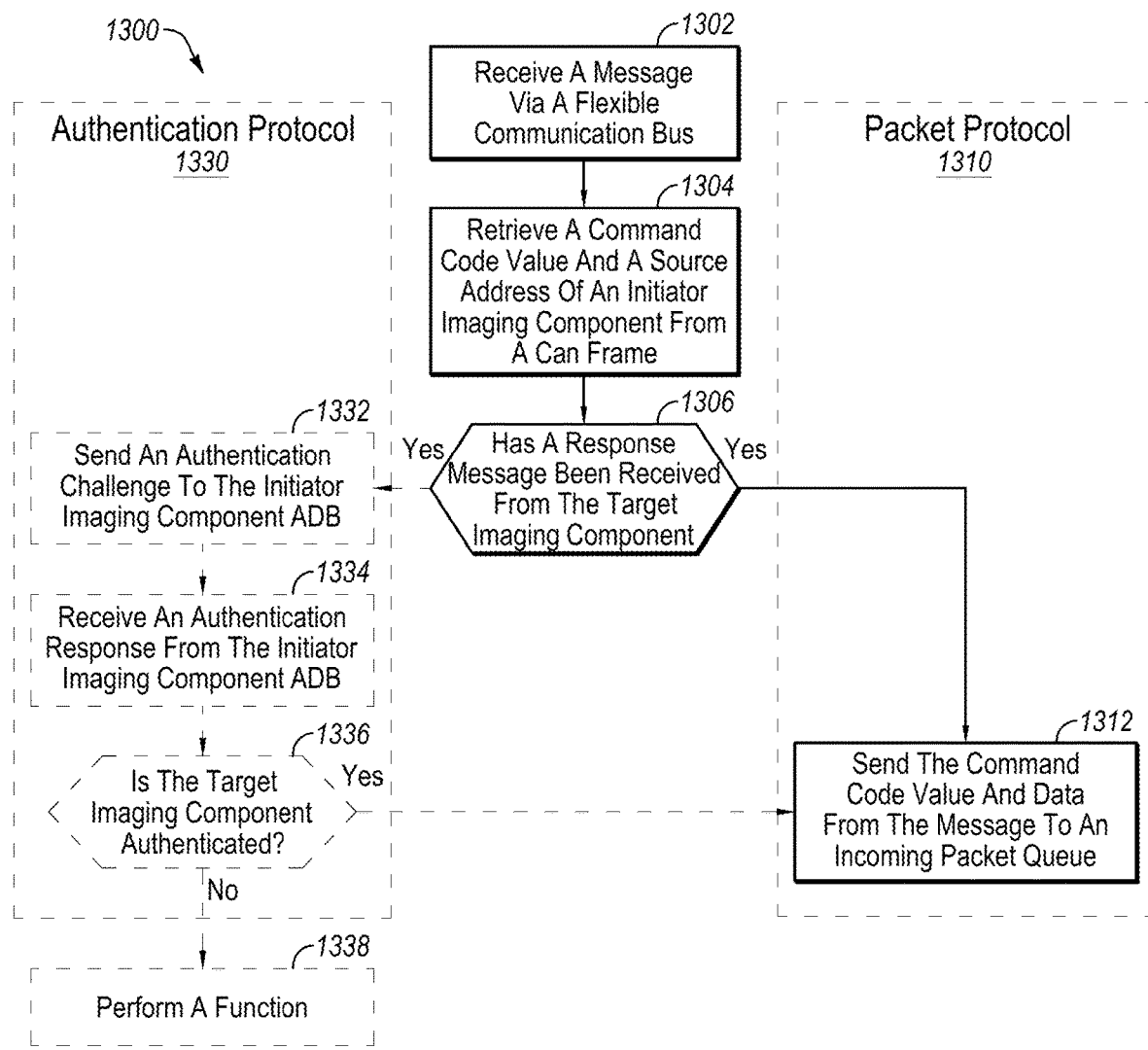
FIG. 13 is a flow chart illustrating an example method for sending a message using a packet protocol and authenticating an SMIC according to an authentication protocol.

FIG. 13 is a flow chart illustrating an example method 1300 for receiving a message using a packet protocol 1310 and authenticating an SMIC according to an authentication protocol 1330, according to one or more embodiments disclosed herein. The method 1300 may be performed by any suitable system, apparatus, or imaging component. For example, the systems 600 and 700 of FIGS. 6 and 7 may direct performance of one or more of the operations associated with the method 1300. Although illustrated with discrete blocks, the steps and operations associated with one or more of the blocks of the method 1300 may be divided into additional blocks, combined into fewer blocks, or eliminated, depending on the particular implementation. Communicating using the packet protocol may include generating messages according to the packet protocol.

The method 1300 may begin at block 1302, in which the message may be received via a flexible communication bus. In some embodiments, the message may include a communication packet and an initiator imaging component may include a SMIC. In one embodiment, the flexible communication bus may be the same as or similar to the flexible communication bus 764 discussed above in relation to FIG. 4. Following block 1302, the method 1300 may proceed to block 1304.

At block 1304, a command code value and a source address of the initiator imaging component may be retrieved from a CAN frame. The CAN frame may correspond to the message. In some embodiments, the command code value may be included in a SM command code field in the communication packet. In these and other embodiments, the SM command code field may be the same as or similar to the SM command code field 338 discussed above in relation to FIG. 3. In other embodiments, the command code value may be included in a PM command code field in the header packet or a data packet. In these and other embodiments, the PM command code field may be the same as or similar to the PM command code field 454 discussed above in relation to FIG. 4 and/or FIG. 5. Following block 1304, the method 1300 may proceed to block 1306.

At block 1306, it may be determined whether the command code value in the message is associated with a SMIC. For example, the command code value in the message may be compared to the PM command code values and the SM command code value discussed above in relation to Table II and Table III. If the command code value in the message is the same as or similar to one of the PM command code values in Table III, the command code value may not be associated with a SMIC. If the command code value in the message is the same as or similar to the SM command code value in Table II, the command code value may be associated with a SMIC.

In response to determining that the command code value is not associated with a SMIC, the method 1300 may end. In response to determining that the command code value is associated with a SMIC, in some embodiments, the initiator imaging component may be authenticated, when the initiator imaging component is to be authenticated, the method 1300 may proceed to block 1332. In some embodiments, the operations of blocks 1332, 1334, and 1336 may be performed according to the authentication protocol 1330. The authentication protocol 1330 may be the same as or similar to the message protocol discussed elsewhere in the present disclosure.

In response to determining that the command code value is associated with a SMIC, in other embodiments, when the initiator imaging component is not to be authenticated, the method 1300 may proceed to block 1312. In some embodiments, the operations of block 1312 may be performed according to the packet protocol 1310. The packet protocol 1310 may be the same as or similar to the packet protocol discussed elsewhere in the present disclosure. At block 1312, the command code value and data from the message may be sent to an incoming packet queue.

At block 1332, an authentication challenge may be sent to an initiator imaging component ADB. Block 1332 may be similar or comparable to block 1232 of method 1200. Following block 1332, the method 1300 may proceed to block 1334.

At block 1334, an authentication response from the target imaging component ADB may be received. Block 1334 may be similar or comparable to the block 1234 of method 1200. Following block 1334, the method 1300 may proceed to block 1336.

At block 1336, it may be determined whether the target imaging component is authenticated. Block 1336 may be similar or comparable to block 1236 of method 1200.

In response to the target imaging component being authenticated, the method 1300 may proceed to block 1312. In response to the target imaging component not being authenticated, the method 1300 may proceed to block 1338. At block 1338, a function may be performed.

In some configurations, an X-ray imaging system (600, 700) may include a TCU (604). The TCU (604) may be configured to communicate via a packet protocol and a message protocol. The X-ray imaging system (600, 700) may also include a SMIC (766). The SMIC (766) may be configured to communicate via the packet protocol. The X-ray imaging system (600, 700) may additionally include a PMIC (762). The PMIC (762) may be configured to communicate via at least one of the message protocol and the packet protocol. The X-ray imaging system (600, 700) may include a flexible communication bus (764). The flexible communication bus (764) may communicatively couple the TCU (604), the SMIC (766), and the PMIC (463). The TCU (604) may be configured to communicate with the SMIC (766) via the flexible communication bus (764) by way of the packet protocol. The TCU (604) may also be configured to communicate with the PMIC (762) via the flexible communication bus (764) by way of the message protocol. The PMIC (762) may be configured to communicate with the SMIC (766) via the flexible communication bus (764) by way of the packet protocol In some configurations, the packet protocol may include a communication packet (300) including a communication packet identifier portion (330) and a communication packet data portion (332). The communication packet identifier portion (330) may include a source field (334), a destination field (336), a SM command code field (338), and a packet number field (340). The communication packet data portion (332) may include one or more data fields (342*a*-342*f*) and one or more command fields (344*a*-344*b*).

In some configurations, the message protocol may include a header packet (400) and one or more data packets (500). The header packet (400) may include a header packet identifier portion (446) and a header packet data portion (448). The header packet data portion (448) may include one or more CRC fields (458*a*, 458*b*), an encryption field (460), a response code field (462), an acknowledge field (464), and a total message data bytes field (466, 468).

In some configurations, the one or more data packets (500) may include a data packet identifier portion (870) and a data packet data portion (872). The data packet identifier portion (870) may include a PM source field (450), a PM destination field (452), a PM command code field (454), a packet number field (340) and a data packet number field (574). The PM source field (450) may include a component ID associated with at least one of the TCU (604), the SMIC (766), and the PMIC (762).

In some configurations, the TCU (604) and the PMIC (762) may be manufactured by a first manufacturer and the SMIC (766) may be manufactured by a second manufacturer. The flexible communication bus (764) may be at least one of a CAN bus, a TCP/IP bus, an I2C bus, or an SPI bus.

In some configurations, the X-ray imaging system may also include a target imaging component authentication daughter board (720) associated with the SMIC (766). The target imaging component authentication daughter board (720) may be configured to communicate via the message protocol. The flexible communication bus (764) may communicatively couple the target imaging component authentication daughter board (720) and the TCU (604). The TCU (604) may also be configured to communicate with the target imaging component authentication daughter board (720) via the flexible communication bus (764) by way of the message protocol.

The terms and words used in the above description and following claims are not limited to the bibliographical meanings, but, are merely used to enable a clear and consistent understanding of the disclosure. It is to be understood that the singular forms "a," "an," and "the" include plural referents unless the context clearly dictates otherwise. Thus, for example, reference to "a component surface" includes reference to one or more of such surfaces.

The embodiments described in this disclosure may include the use of a special purpose or general-purpose computer including various computer hardware or software modules, as discussed in greater detail below.

Embodiments within the scope of this disclosure also include computer-readable media for carrying or having computer-executable instructions or data structures stored thereon. Such computer-readable media can be any available media that can be accessed by a general purpose or special purpose computer. By way of example, and not limitation, such computer-readable media can comprise random-access memory (RAM), read-only memory (ROM), electrically erasable programmable read-only memory (EEPROM), compact disc read-only memory (CD-ROM) or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions.

As used herein, the term "module" or "component" can refer to software objects or routines that execute on the computing system. The different components and modules described herein may be implemented as objects or processes that execute on the computing system (e.g., as separate threads). While the system and methods described herein may be implemented in software, implementations in hardware or a combination of software and hardware are also possible and contemplated. In this description, a "computer" or "computer system" may be any suitable computing system as previously defined herein, or any module or combination of modules running on a computing system.

For the processes and/or methods disclosed, the functions performed in the processes and methods may be implemented in differing order as may be indicated by context. Furthermore, the outlined steps and operations are only provided as examples, and some of the steps and operations may be optional, combined into fewer steps and operations, or expanded into additional steps and operations.

This disclosure may sometimes illustrate different components contained within, or connected with, different other components. Such depicted architectures are merely exemplary, and many other architectures can be implemented which achieve the same or similar functionality.

Aspects of the present disclosure may be embodied in other forms without departing from its essential characteristics. The described aspects are to be considered in all respects illustrative and not restrictive. The claimed subject matter is indicated by the appended claims rather than by the foregoing description. All changes which come within the meaning and range of equivalency of the claims are to be embraced within their scope.

What is claimed is:

1. A method of communicating between imaging components of an X-ray imaging system; the method comprising:
   determining, by an initiator imaging component, whether a target imaging component is a primary manufacturer imaging component;
   responsive to the target imaging component not being a manufacturer imaging component:
      generating a communication message including a communication packet according to a packet protocol; and
      sending the communication message to the target imaging component as a secondary manufacturer imaging component; and
   responsive to the target imaging component being the primary manufacturer imaging component:
      generating a message including a header packet and one or more data packets according to a message protocol; and
      sending the message to the target imaging component as the primary manufacturer imaging component.

2. The method of claim 1, wherein generating the communication message including the communication packet further comprises:
   setting a value of a communication packet identifier portion and a communication packet data portion in the communication packet according to the packet protocol, prior to generating the communication message including the communication packet; and wherein generating the message including the header packet and one or more data packets further comprises:
   setting a value of a header packet identifier portion and a header packet data portion in the header packet according to the message protocol.

3. The method of claim 2, wherein setting the value of the communication packet identifier portion in the communication packet includes using a first predetermined value of a command code field and setting the value of the header packet identifier portion in the header packet includes using a second predetermined value of the command code field that is different from the first predetermined value.

4. The method of claim 2, wherein when the target imaging component is a secondary manufacturer imaging component, the method further comprising:
   sending, by the target imaging component, packet command and data included in the message to an incoming packet queue; and wherein
   when the target imaging component is the primary manufacturer imaging component, the method further comprising:
      determining, by the target imaging component, whether a frame of a current packet is a header frame;
      responsive to the frame being the header frame:
         obtaining header data from the header packet; and
      responsive to the frame not being the header frame:
         performing a command included in the message.

5. The method of claim 2, wherein the target imaging component is the primary manufacturer imaging component and setting the value of the communication packet identifier portion in the communication packet according to the packet protocol further comprises:
   setting a value in a secondary manufacturer command code field in the communication packet identifier portion to a command code to indicate the target imaging component is the secondary manufacturer imaging component; and
   setting a command field in the communication packet data portion to include a command code value to request a function on the secondary manufacturer imaging component.

6. The method of claim 2, wherein the target imaging component is a first primary manufacturer imaging component, and setting the value of the header packet identifier portion in the header packet according to the message protocol further comprises:
   setting a value in a primary manufacturer command code field to a command code to indicate the target imaging component is a second primary manufacturer imaging component, wherein the value in the primary manufacturer command code field also requests a function on the second primary manufacturer imaging component; and
   setting a data packet data portion in the one or more data packets to include data associated with the value in the primary manufacturer command code field to be sent to the second primary manufacturer imaging component.

7. The method of claim 1, wherein the packet protocol provides open communication between imaging components and the message protocol provides secure communication between primary manufacturer imaging components.

8. The method of claim 1, wherein the target imaging component is a first primary manufacturer imaging component and the initiator imaging component is a second primary manufacturer imaging component.

9. The method of claim 1, wherein the target imaging component is a secondary imaging component, the method further comprising:
   receiving a second communication message from the target imaging component using the packet protocol;
   sending an authentication challenge according to the message protocol to a target imaging component authentication daughter board associated with the target imaging component;
   receiving an authentication response, from the target imaging component authentication daughter board according to the message protocol; and
   determining, by the initiator imaging component, whether the target imaging component is authenticated based on the authentication response, wherein the second communication message is sent to component incoming message queue for processing responsive to the target imaging component being authenticated.

10. A non-transitory computer-readable storage medium having stored thereon instructions that when executed by a machine result in operation of the method of claim 1.

11. An X-ray imaging system comprising:
   a tube control unit configured to communicate via a packet protocol and a message protocol;
   a secondary manufacturer imaging component configured to communicate via the packet protocol;

a primary manufacturer imaging component configured to communicate via at least one of the message protocol and the packet protocol; and a flexible communication bus communicatively coupling the tube control unit, the secondary manufacturer imaging component, and the primary manufacturer imaging component, wherein the tube control unit is configured to communicate with the secondary manufacturer imaging component via the flexible communication bus by way of the packet protocol and the primary manufacturer imaging component via the flexible communication bus by way of the message protocol, and the primary manufacturer imaging component is configured to communicate with the secondary manufacturer imaging component via the flexible communication bus by way of the packet protocol.

12. The X-ray imaging system of claim 11, wherein the packet protocol comprises a communication packet comprising a communication packet identifier portion and a communication packet data portion, and the message protocol comprises a header packet and one or more data packets, each including a packet identifier portion and a packet data portion.

13. The X-ray imaging system of claim 12, wherein the communication packet identifier portion comprises a source field; a destination field, a secondary manufacturer command code field, and a packet number field, and the communication packet data portion comprises one or more data fields and one or more command fields.

14. The X-ray imaging system of claim 12, wherein the packet identifier portion and the packet data portion comprises one or more cyclic redundancy check (CRC) fields, an encryption field, a response code field, an acknowledge field, and a total message data bytes fields.

15. The X-ray imaging system of claim 12, wherein packet identifier portion of the header packet and the one or more data packets comprise a primary manufacturer source field, a primary manufacturer destination field, a primary manufacturer command code field, a packet number field, and a data packet data portion.

16. The X-ray imaging system of claim 15, wherein the primary manufacturer source field comprises a component identification (ID) associated with at least one of the tube control unit, the secondary manufacturer imaging component, and the primary manufacturer imaging component.

17. The X-ray imaging system of claim 12, wherein the tube control unit and the primary manufacturer imaging component are manufactured by a first manufacturer and the secondary manufacturer imaging component is manufactured by a second manufacturer and the flexible communication bus includes at least one of a controller area network (CAN) bus, a transmission control protocol/Internet Protocol (TCP/IP) bus, inter-integrated circuit (I2C) bus, or serial peripheral interface (SPI) bus.

18. The X-ray imaging system of claim 11, the X-ray imaging system further comprises a target imaging component authentication daughter board associated with the secondary manufacturer imaging component, wherein the target imaging component authentication daughter board is configured to communicate via the message protocol, the tube control unit is further configured to communicate via the message protocol, the flexible communication bus communicatively couples the target imaging component authentication daughter board and the tube control unit, and the tube control unit is further configured to communicate with the target imaging component authentication daughter board via the flexible communication bus by way of the message protocol.

19. A system including a means for:

determining, by an initiator imaging component, whether a target imaging component is a primary manufacturer imaging component;

responsive to the target imaging component not being the primary manufacturer imaging component:
generating a communication message including a communication packet according to a packet protocol; and
sending the communication message to the target imaging component as a secondary manufacturer imaging component; and responsive to the target imaging component being the primary manufacturer imaging component:
generating a message including a header packet and one or more data packets according to a message protocol; and
sending the message to the target imaging component as the primary manufacturer imaging component.

20. The system of claim 19, wherein the means for generating the communication message including the communication packet further comprises:
setting a value in a secondary manufacturer command code field in a communication packet identifier portion in the communication packet to a command code to indicate the target imaging component is the secondary manufacturer imaging component according to the packet protocol and a value in a command field in a communication packet data portion in the communication packet to include a command code value to request a function on the secondary manufacturer imaging component according to the packet protocol, prior to generating the communication message including the communication packet; and wherein the means for generating the message including the header packet and one or more data packets further comprises:
setting a value of a header packet identifier portion and a header packet data portion in the header packet according to the message protocol.

* * * * *